United States Patent

Powers et al.

[11] Patent Number: 5,810,789
[45] Date of Patent: Sep. 22, 1998

[54] CATHETERS WITH NOVEL LUMEN SHAPES

[75] Inventors: Kelly B. Powers, North Salt Lake City; Kelly J. Christian, Sandy; Kenneth Arden Eliasen, Murray; Ronald O. Campbell, Farmington; Donald James Jones, West Valley City; Kris Flanary, Orem, all of Utah

[73] Assignee: C. R. Bard, Inc., Murray Hill, N.J.

[21] Appl. No.: 628,377

[22] Filed: Apr. 5, 1996

[51] Int. Cl.$^6$ ................................................ A61M 25/00
[52] U.S. Cl. ............................ 604/280; 604/43; 604/247
[58] Field of Search .......................... 604/43, 246, 247, 604/264, 280

[56] References Cited

U.S. PATENT DOCUMENTS

| | | |
|---|---|---|
| 883,583 | 3/1908 | Stallsmith . |
| 4,406,656 | 9/1983 | Hattler et al. ............................ 604/280 |
| 4,619,643 | 10/1986 | Bai ............................................. 604/43 |
| 4,643,711 | 2/1987 | Bates ........................................... 604/4 |
| 4,668,221 | 5/1987 | Luther ..................................... 604/164 |
| 4,671,796 | 6/1987 | Groshong et al. ...................... 604/247 |
| 4,753,640 | 6/1988 | Nichols et al. ......................... 604/247 |
| 4,790,817 | 12/1988 | Luther ....................................... 604/53 |
| 4,795,439 | 1/1989 | Guest ........................................ 604/43 |
| 4,995,863 | 2/1991 | Nichols et al. ......................... 604/247 |
| 5,135,599 | 8/1992 | Martin et al. ........................... 156/294 |
| 5,156,590 | 10/1992 | Vilmar ........................................ 604/4 |
| 5,160,325 | 11/1992 | Nichols et al. ......................... 604/247 |
| 5,221,256 | 6/1993 | Mahurkar ................................. 604/43 |
| 5,378,230 | 1/1995 | Mahurkar ................................. 604/43 |
| 5,395,316 | 3/1995 | Martin ..................................... 604/43 |

FOREIGN PATENT DOCUMENTS 1383989   9/1966   France .

OTHER PUBLICATIONS

Davol Speciality Access Products, *Patient Information Manual for Groshong™ Catheter* (1991).

Bard Access Systems, *Hickman® Catheters* (1994).

Bard Access Systems, *Groshong® Catheters* (1996).

*Primary Examiner*—Corrine M. McDermottt
*Attorney, Agent, or Firm*—Trask, Britt & Rossa

[57] ABSTRACT

Vascular access catheters that include a catheter body having one or a plurality of lumens longitudinally extending therethrough. The lumens have cross-sectional shapes that enhance kink resistance, support reliable slit valve operation, and couple securely with the outlet stem of a multiple reservoir implantable access port. In a dual lumen catheter disclosed, each of the lumens are defined by a plurality of longitudinally extending generally linear inner wall surfaces. The inner wall surfaces when viewed in a transverse cross section of the catheter body taken normal to the longitudinal access have trapezoidal shapes. Other cross-sectional shapes are also illustrated. A generally planar septum separates the pair of lumens. The lumens effect a fluid-tight mechanical engagement between the D-shaped outlet prongs of a conventional outlet stem of an implantable dual reservoir access port, highly reliable two-way, three-position slit valves may be associated with each of the lumens. The valve for each lumen has a closed position thereof in which fluid communication is precluded between the lumen and the exterior of the catheter body, but the valve is selectively operable under the influence of appropriate pressure differentials between the lumens and the exterior of the catheter from the closed position into either an inwardly or an outwardly open position.

83 Claims, 17 Drawing Sheets

CATHETERS WITH NOVEL LUMEN SHAPES

BACKGROUND

1. The Field of the Invention

This invention pertains to medical catheters, and more particularly to catheters adapted for transcutaneous or complete implantation in human medical patients to provide access through the catheter to the cardiovascular system of the patient.

2. Background Art

The use of medical catheters to access the cardiovascular system of a patient is increasingly common. The vascular access afforded through such catheters permits the monitoring of blood pressure, the sampling of blood, and the infusion of medicaments and nutrients at locations that are central to the cardiovascular system, in the vicinity of the high volume blood flow passageways immediately interconnected with the heart.

Vascular access catheters of this type are implanted in the body of a patient with the distal end of the catheter positioned at an intended location in one of these central venous locations. The majority of the length of the catheter proximal thereof resides in the contiguous blood vessels leading away from the heart. In this manner the proximal end of such vascular access catheters can exit the cardiovascular system remote from the heart, thereby to be accessible to medical practitioners at locations that are distant from delicate viscera.

Increasing experience with such practices has lead to the development of highly specialized, technologically sophisticated vascular access catheters designed to meet the needs associated with specific therapeutic procedures.

FIG. 1 illustrates one such procedure in which remote access is provided on a repeated long-term basis to the superior vena cava 10 of the cardiovascular system of a patient 12. The access is provided through the implantation of a vascular access system 14 that includes a soft biocompatible dual lumen vascular access catheter 16, a pair of access tubes 18 associated individually with a corresponding one the lumens in catheter 16, and a bifurcation hub 20 by which each of access tubes 18 is placed in fluid communication with the corresponding of the lumens in catheter 16. The distal end 22 of catheter 16 resides in superior vena cava 10 as shown. The proximal end 24 of the catheter 16 exits the cardiovascular system and traverses the skin of the patient to the exterior of the body thereof in the vicinity of the shoulder 26. Proximal end 24 of catheter 16 is open-ended to provide fluid communication with each of access tubes 18. Bifurcation hub 20 and access tubes 18 thus remain external to the body of patient 12, affording direct external access to proximal end 24 of catheter 16.

FIG. 2 is an enlarged perspective view of distal end 22 of catheter 16 shown in FIG. 1. There catheter 16 can be seen to terminate in a rounded distal tip 28 that is closed. Proximal end 24 of catheter 16 is by contrast considered open despite the termination of proximal end 24 in bifurcation hub 20.

Each of the lumens formed through catheter 16 communicates on a selected basis with the exterior of distal end 22 of catheter 16 through a respective two-way, three-position valve that is associated with each lumen at distal end 22 of catheter 16. Such a valve is illustrated in FIG. 2 as being a slit valve 30 shown in the closed position thereof in which fluid communication is precluded between the exterior of catheter 16 and the lumen therein with which slit valve 30 is associated.

As can be appreciated by reference to the transverse cross section of catheter 16 shown in FIG. 3, a similar slit valve is associated with the other lumen in catheter 16. There slit valve 30 will be appreciated to be associated with a first lumen 32 longitudinally disposed through catheter 16, while a second lumen 34 has associated therewith a slit valve 36. Each of slit valve 30 and slit valve 36 is selectively operable in response to appropriate pressure differentials between the lumen associated therewith and the exterior of catheter 16. Such pressure differentials move the elements of the slit valves out of the closed position thereof illustrated in FIG. 3 into either an outwardly or an inwardly open position in which each of fluid communication and flow is enabled.

It has been empirically determined that the shape of the lumen with which a slit valve is associated in a dual lumen catheter quite decisively affects the quality of the functioning of the slit valve. Notably, reliable slit valve operation has come to be associated with lumens having cross-sectional configurations such as those illustrated in first lumen 32 and second lumen 34 in FIG. 3. As seen there, the cross section of each of first lumen 32 and second lumen 34 is substantially square. Thus, the cross section of first lumen 32 comprises generally linear inner wall surfaces 38, 39, 40, and 41, adjacent pairs of which are interconnected by rounded corners 42.

Slit valve 30 is formed through the material of catheter 16 in an asymmetrical relationship to inner wall surface 38, proximate to corner 42 between inner wall 38 and inner wall 39. The cross section of second lumen 34 is geometrically similar in shape but smaller in size than the cross section of first lumen 32. First lumen 32 and second lumen 34 are not, therefore, geometrically congruent. Slit valve 36 is similarly asymmetrically formed through the material of catheter 16 relative to the cross section of second lumen 34.

The lumen shapes and asymmetrical dispositions of slit valves relative thereto as illustrated in FIG. 3 have proved to be highly advantageous in producing reliable slit valve operation, and therefor for permitting the selective, safe infusion or withdrawal of fluids. The noncircular cross section of first lumen 32 and of second lumen 34 is thus motivated toward achieving optimum operation of any slit valves associated with these lumens. Nonetheless, these asymmetrical shapes in the lumens present a challenge in coupling the proximal ends of such lumens to related medical devices that are actually used to infuse or withdraw those fluids. This challenge is overcome in vascular access system 14 shown in FIG. 1 through the use of an injection molded hub, such as bifurcation hub 20, which accommodates the square cross section of first lumen 32 and second lumen 34 to the circular interior passageway in each of access tube 18. Access tubes 18 are each provided with clamps, luer lock connectors, and caps as are appropriate to the medical purpose intended for vascular access system 14.

Despite the manifest convenience in accessing the central vascular access system repeatedly using vascular access system 14, certain deficiencies therein have been noted. For example, the presence on the outside of the body of a patient of exposed components, such as access tubes 18 or bifurcation hub 20 of vascular access system 14, offer obstructions to the easy donning of clothing or the wearing of close fitting garments. The presence of such exposed elements of a vascular access system are often troubling to third parties and contribute to a morbid fixation even in the patient.

In addition, the utilization of structure such as access tubes 18 to terminate the proximal ends of lumens in vascular access catheters requires the active use of structures such as clamps and caps to ensure that external access to the lumens in such catheters is sealed from leakage and infection when the lumens are not in use. The operation of such structures requires conscientious actions on the part of medical personnel or the patient. correspondingly, lapses of attention by such individuals presents the risks of inadvertent hemorrhage or infection.

Finally, externally accessible components of a vascular access system are susceptible by accident or repeated use to breakage and damage. This raises anew concerns of leakage and infection, and requires attention to the development of repair technology for any such broken components.

Accordingly, a second form of vascular access system 44 has been developed that is shown in FIG. 4 implanted in the body of a patient 45. Vascular access system 44 includes a soft biocompatible dual lumen vascular access catheter 46 that is implanted with the distal end 47 thereof resident in the superior vena cava 48 of patient 45. The proximal end 49 of catheter 46 is mechanically coupled in fluid-tight communication with an implantable dual reservoir access port 50.

Significantly, all elements of vascular access system 14 shown in FIG. 1, including access port 50, are fully implantable in the body of patient 45. Access to the proximal end of the lumens in catheter 46 is afforded transcutaneously on a selected basis utilizing a hypodermic syringe 52. Syringe 52 penetrates the skin of patient 45 at the implantation site for access port 50 and then passes through a selected one of either of a pair of needle-penetrable septums 54 that seal respective of the fluid reservoirs within access port 50.

In a vascular access system, such as vascular access system 44, the inconvenience presented by exposed elements of a vascular access system is eliminated. The need for attention in closing the proximal access to the lumens in the catheter of such a vascular access system is no longer present. Breakage of components due to repeated external manipulation or accident is also not present.

Nonetheless, the advantages of vascular access system 44 of FIG. 4 relative to vascular access system 14 of FIG. 1 are obtained at some expense to other performance aspects of the system.

Some of these disadvantageous consequences are best illustrated by reference to FIG. 5. There the elements of vascular access system 44 are shown disassembled from each other and removed from the body of patient 45. Therefore, in FIG. 5 it can be seen that the mechanical attachment of catheter 46 to access port 50 is effected utilizing an outlet stem 56 that projects outwardly from the body of access port 50 and includes a pair of parallel, open-ended outlet prongs 58, 59. Each of outlet prongs 58, 59 encloses a passageway that communicates respectively with one of the fluid reservoirs within access port 50. To mechanically secure catheter 46 to access port 50, proximal end 49 of catheter 46 is advanced onto outlet prongs 58, 59 and secured thereon by sliding a cylindrical locking sleeve 60 along catheter 46 toward access port 50 into the position illustrated in FIG. 5.

Since outlet prongs 58, 59 of outlet stem 56 are advanced into proximal end 49 of catheter 46 in effecting this mechanical interconnection, the structure of outlet prongs 58, 59 requires an accommodating configuration of the cross section of the lumens in catheter 46. Accordingly, a closer investigation of the outer structure of typical outlet prongs, such as outlet prongs 58, 59 is appropriate. In FIG. 6 each of outlet prongs 58, 59 is seen to have an inner surface that opposes the other of the outlet prongs. The inner surface of each is substantially planar. Thus, outlet prong 58 has a planar inner surface 62 shown only in FIG. 6, while outlet prong 59 has a planar inner surface 64 shown only in FIG. 5.

As outlet prongs 58, 59 are parallel, inner surface 62 and inner surface 64 define therebetween a longitudinal slot 66 shown in FIG. 6 as having a thickness $T_S$ and a width $W_S$. In an alternative embodiment, inner wall surfaces 62 and 64 may taper slightly so that thickness $T_S$ is slightly smaller adjacent to the body of access port 50 than at the free distal end of outlet stem 56. As used in this specification and the appended claims however such configurations of stem 56 are considered as having parallel outlet prongs with substantially planar inner surfaces opposing each other.

The width $W_S$ of slot 66 is equal to the width of inner surface 62 of outlet prong 58 or the width of inner surface 64 of outlet prong 59. It is also apparent from FIG. 6 that the outer surface 68 of outlet prong 58 and the outer surface 69 of outlet prong 59 are semi-cylindrical. Thus, each of outlet prongs 58, 59 has a D-shaped transverse cross section that is replicated in the distal face 70 of outlet prong 58 and the distal face 72 of outlet prong 59.

The implications of the cross-sectional shape of outlet prongs 58, 59 are directly reflected in the cross-sectional configuration of the lumens 76, 78 formed through catheter 46 and shown in enlarged perspective in FIG. 5. Lumens 76, 78 exhibit D-shaped cross sections that are imitative of the cross section of outlet prongs 58, 59. The flat inner wall surface of the cross section of lumen 76 and the cross section of lumen 78 are arranged opposing each other, thereby to define between lumens 76, 78 a substantially planar septum 80.

When proximal end 49 of catheter 46 is advanced onto outlet stem 56, outlet prong 58 enters, for example, lumen 76, while outlet prong 59 enters lumen 78. Correspondingly, septum 80 of catheter 46 is received between planar inner surface 62 of outlet prong 58 and planar inner surface 64 of outlet prong 59, substantially filling longitudinal slot 66. A satisfactory mechanical and fluid coupling is thus effected between the lumens of catheter 46 and the fluid reservoirs within access port 50.

Nonetheless, the D-shaped cross section that results in lumens 76, 78 of catheter 46 produces an overall catheter cross section that has been determined empirically to be less than optimally suited for utilization with valves, such as slit valves 30, 36 that are employable with the closed distal tip 28 of catheter 16 in vascular access system 14 shown in FIG. 1.

Consequently, distal end 47 of catheter 46 as shown in FIG. 5 must be open-ended. In open-ended catheters, access to the lumens of the catheter by the fluids in the cardiovascular system cannot be readily controlled during the periods when the lumens of the catheter are not in use. This can lead to a build-up of contaminants, such as thrombosis, that can block the lumens and also affords refuge for infectious bacteria.

Furthermore, experience in the use of vascular access catheters has also lead to an appreciation that such catheters, when made of an extremely soft biocompatible material, such as silicone rubber, can readily kink, even during residence in the blood vessels of the cardiovascular system. Kinking can have calamitous consequences by totally obstructing fluid flow in one or all lumens in an implanted catheter. While the problem of kinking is less pronounced in catheters, such as catheter 16 shown in FIG. 3 having lumens with square cross-sectional shapes, the kink resistance in catheters with lumens having D-shaped cross sections is relatively discouraging.

As a result, the advantageous utilization of a catheter with a closed distal tip has to date necessarily been unobtainable where the catheter involved is, by attachment to an implantable access port, intended to be utilized in a totally implantable vascular access system.

SUMMARY OF THE INVENTION

Accordingly, one object of the present invention is an improved catheter for a vascular access system that eliminates the disadvantages of externally exposed structures of the implanted system, while reserving the capacity of the system to employ a catheter with a closed distal tip.

More specifically, it is an object of the present invention to provide a vascular access catheter that eliminates inconvenience, risk, and maintenance associated to externally exposed components of a vascular access system, while nonetheless employing at the distal end of the catheter a highly reliable two-way, three-position valving structure.

Another object of the present invention is to enable the use with implantable access ports of vascular access catheters having closed distal tips.

Yet another object of the present invention is that of permitting the use of two-way, three-position valving structures, such as slit valves, in conjunction with implantable access ports, but without the need to reconfigure the outlet stems currently used with such access ports.

Still another object of the present invention is to provide a vascular access catheter made of soft biocompatible silicone that exhibits enhanced kink resistance relative to dual lumen catheters having D-shaped lumens separated by a planar septum.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a dual lumen catheter is provided. The catheter is implantable in the body of a patient in fluid communication with the fluid reservoirs of a dual reservoir access port. The access port has an outlet stem that includes a pair of parallel outlet prongs projecting outwardly from the body of the access port. Each of the outlet prongs has an inner surface opposing the other of the outer prongs. As a result, the planar inner surfaces of the outlet prongs define a slit in the outlet stem.

The dual lumen catheter comprises an elongated catheter body of elastomeric material such as silicone. The catheter body has a longitudinal access, and an exterior surface extending between a proximal end and an opposing distal end. A first lumen longitudinally extends through the catheter body from the proximal end to the distal end. The first lumen is defined by a first set of longitudinally extending inner wall surfaces.

The first lumen, when viewed in a transverse cross section of the catheter body taken normal to the longitudinal access thereof, comprises a generally linear first inner wall surface and a generally linear second inner wall surface. The first inner wall surface is parallel to the second inner wall surface. Furthermore, the length of the first inner wall surface is less than the length of the second inner wall surface. When viewed in the transverse cross-sectional view of the catheter body, the first lumen has a substantially trapezoidal shape.

The inventive catheter also includes a second lumen longitudinally extending through the catheter body from the proximal end to the distal end. The second lumen is defined by a second set of longitudinally extending inner wall surfaces. When viewed in the transverse cross-sectional view of the catheter, the second lumen has a shape substantially similar to the shape of the first lumen. More specifically, the first lumen and second lumen are so configured as to individually receive the parallel outlet prongs from the access port in such a way as to enable a fluid type mechanical joinder therebetween.

In one embodiment, the distal end of the catheter can be opened to freely allow fluids to flow into and out of the first lumen and the second lumen. In an alternative embodiment the distal end can be closed. When the distal end is closed, the catheter may also include a first two-way, three-position valve associated with the first lumen at the distal end of the catheter body. The valve can be biased into a closed position in which fluid communication is precluded between the first lumen and the exterior of the catheter body.

The valve is selectively operable from the closed position thereof into either an inwardly or an outwardly open position. The valve comprises a slit formed in the catheter body extending from the exterior surface thereof to the first lumen. The slit defines opposed first and second slit faces that sealingly engage each other in the closed position of the valve.

The valve further includes a valve wall comprising a portion of the catheter body adjacent to the first slit face. The first valve wall is inwardly flexible into the first lumen in an inwardly open position of the slit valve and outwardly flexible into the exterior of the catheter body in the outwardly open position of the valve.

In an alternative embodiment, a second two-way, three-position valve similar to the first two-way, three-position valve can be associated with the second lumen.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DESCRIPTION OF THE PREFERRED EMBODIMENT

Figure 5:
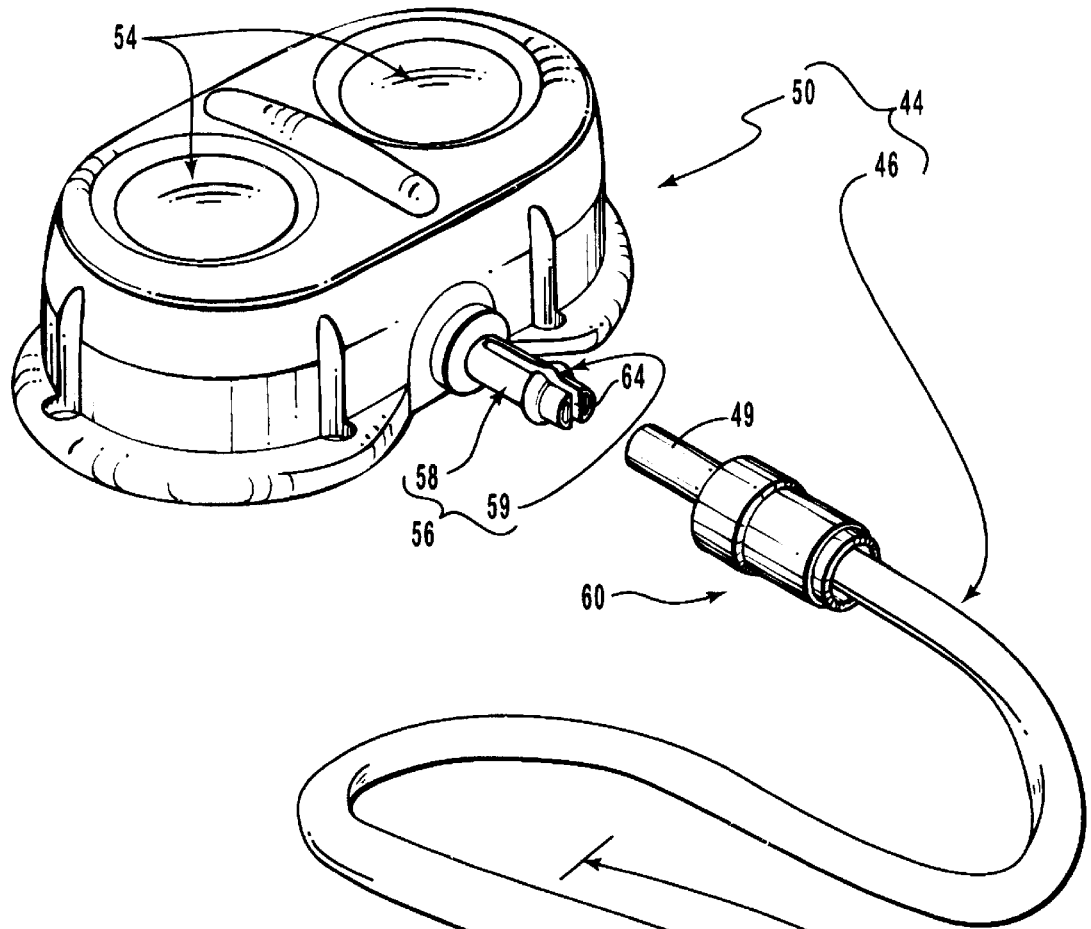
FIG. 5 is an enlarged disassembled perspective view of the dual reservoir access port and the dual lumen catheter of FIG. 4 revealing the outlet stem of that access port and illustrating the cross-sectional configuration of the lumens at the open distal end of that catheter.
Figure 6:
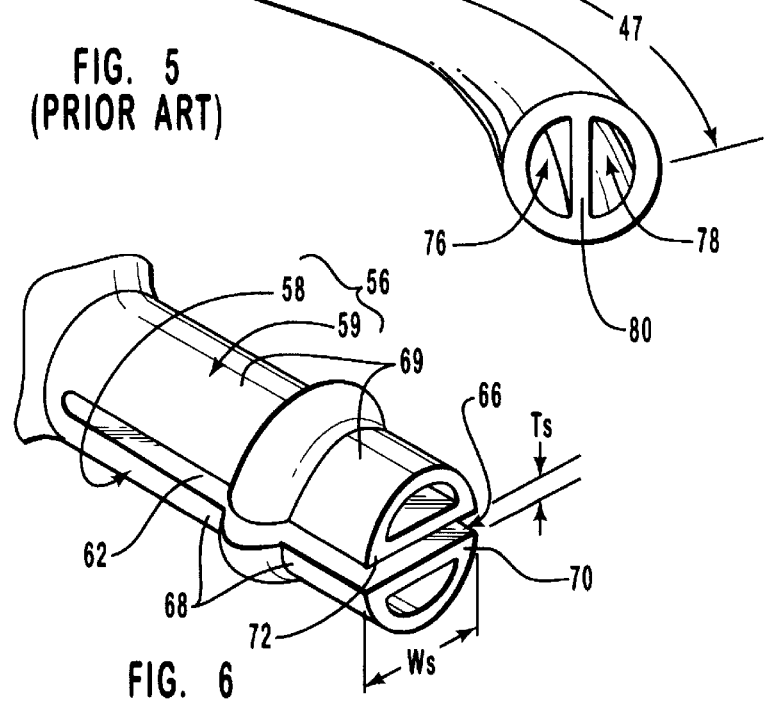
FIG. 6 is an enlarged perspective view of the outlet stem of FIG. 5.
Figure 7:
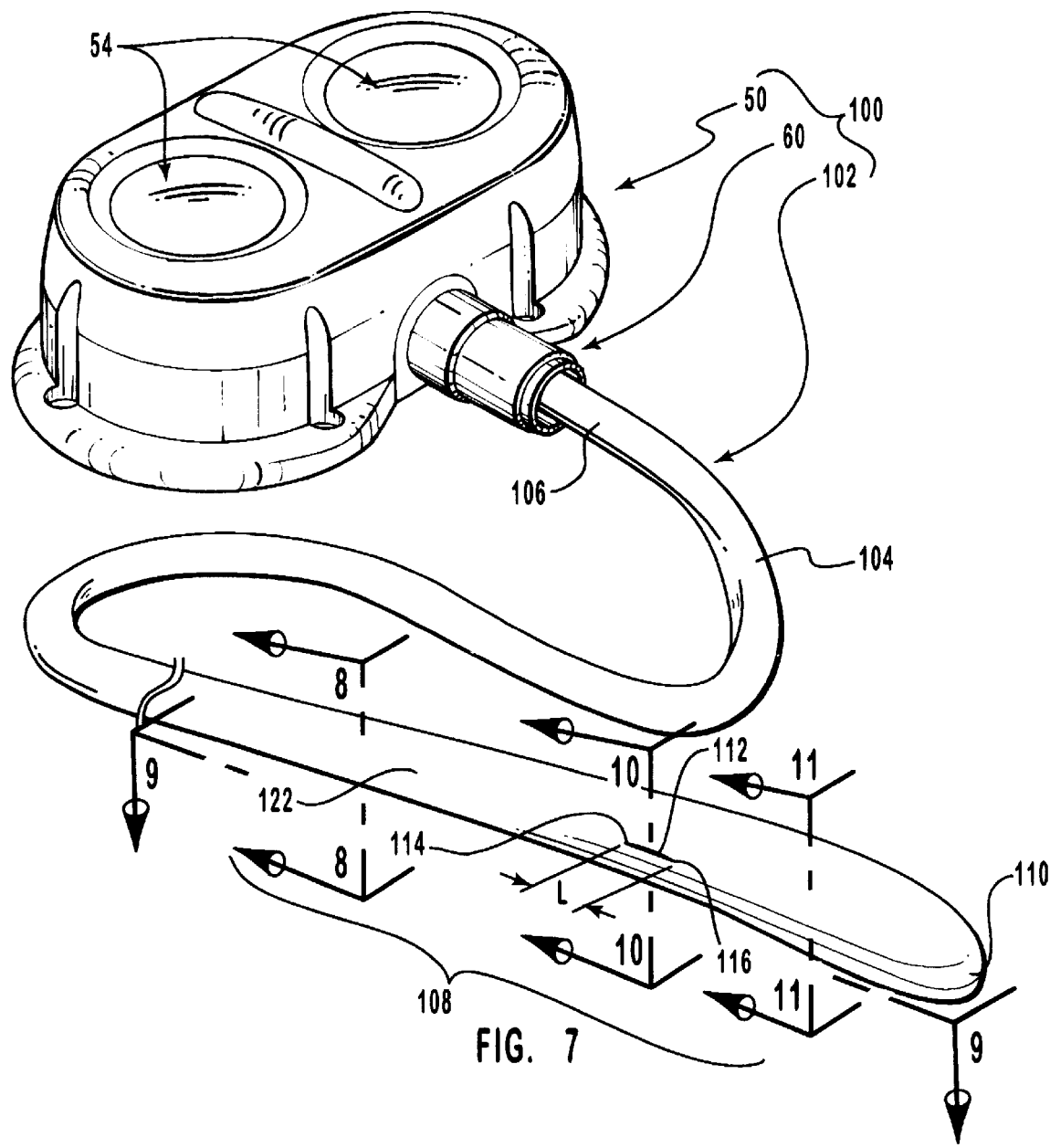
FIG. 7 is a perspective view of a vascular access system including a dual reservoir port and a first embodiment of a dual lumen catheter attached thereto and incorporating teachings of the present invention.

Depicted in FIG. 7 is a vascular access system 100 including access port 50 and a first embodiment of a dual lumen catheter 102 attached thereto and incorporating teachings of the present invention. Catheter 102 is attached to access port 50 by locking sleeve 60 in substantially the same way catheter 46 is attached to access port 50 previously discussed with FIGS. 5 and 6. Access port 50 is only one embodiment of a port that can be used with catheter 102. Any convention dual reservoir port can be used that has a comparable outlet stem 56.

Catheter 102 comprises an elongated, flexible catheter body 122 made from an elastomeric material. The preferred material is silicone having a durometer based on the Shore A Scale in a range between about fifty (50) to about eighty (80) and more preferably in a range between about sixty (60) to about seventy (70). Alternatively, catheter 102 can be made from rubber or other elastomeric biocompatible materials Catheter body 122 has an exterior surface 104 extending from a proximal end 106, attached to access port 50, to an opposing free distal end 108. Distal end 108 terminates at distal tip 110 that is closed to prevent fluid from passing therethrough.

As will be discussed later in greater detail, extending partially through catheter body 122 at distal end 108 is a slit 112. Slit 112 is formed along the longitudinal axis of catheter 102 and has a length "L" that extends from a proximal end 114 to an opposing distal end 116.

Figure 8:
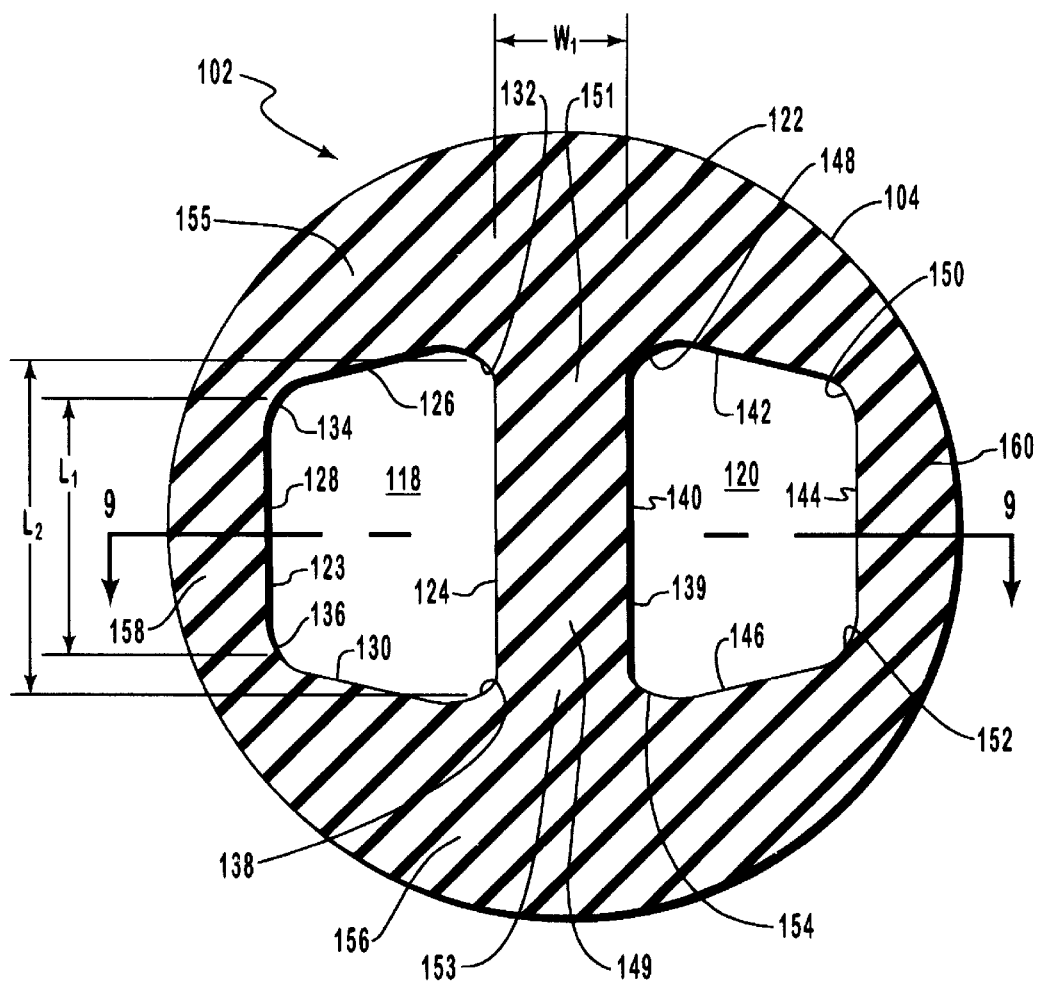
FIG. 8 is a transverse cross-sectional view of the catheter of FIG. 7 taken along section line 8—8 shown therein.

Turning to FIG. 8, a transverse cross-sectional view of catheter 102 taken normal to the longitudinal axis of catheter body 122 is shown taken along section line 8—8. As depicted therein, catheter 102 further comprises a first lumen 118 and an adjacent second lumen 120 formed within catheter body 122. First lumen 118 and second lumen 120 each longitudinally extend from proximal end 106 to distal end 108 of catheter 102. First lumen 118 is defined by an interior surface 123 comprising a generally linear first inner wall surface 128 and an opposing generally linear second inner wall surface 124. First inner wall surface 128 is positioned parallel to second inner wall surface 124.

Interior surface 123 of first lumen 118 further comprises a generally linear connecting inner wall surface 126 and a generally linear connecting inner wall surface 130. Inner wall surfaces 124 and 126 are joined together at a junction 132; inner wall surfaces 126 and 128 are joined together at junction 134; inner wall surfaces 128 and 130 are joined together at a junction 136; and inner wall surfaces 124 and 130 are joined together at a junction 138. Junctions 132, 134, 136 and 138 are depicted as arcuate fillets. Alternative angles, corners or short straight sections can also be used to connect adjacent inner wall surfaces.

Inner wall surface 126 has a length extending between junctions 132 and 134 that is equal to the length of inner wall surface 130 extending between junctions 136 and 138. In contrast, first inner wall surface 128 has a length $L_1$ extending between junctions 134 and 136 that is smaller than the length $L_2$ of second inner wall surface 124 extending between junctions 132 and 138. As a result, first lumen 118 when viewed in a transverse cross section of catheter body 122 taken normal to the longitudinal axis thereof has an isosceles trapezoidal shape. Accordingly, inner wall surfaces 126 and 130 extend between inner wall surfaces 124 and 128 at substantially complementary angles.

Second lumen 120 is shown as having an isosceles trapezoidal shape that is the mirror image of the isosceles trapezoidal shape of first lumen 118. As such, second lumen 120 is defined by an interior surface 139 that also includes a generally linear first inner wall surface 144 that is opposed and parallel to a generally linear second inner wall surface 140. First inner wall surface 144 has a length that is less than the length of second inner wall surface 140.

Interior surface 139 further comprises a generally linear connecting inner wall surface 142 and a generally inner connecting inner wall surface 146. Inner wall surfaces 140 and 142 are joined together at a junction 148; inner wall surfaces 142 and 144 are joined together at a junction 150; inner wall surfaces 144 and 146 are joined together at a junction 152; and inner wall surfaces 146 and 140 are joined together at a junction 154. Junctions 148, 150, 152, and 154 have substantially the same configuration and alternative configurations as discussed with the junctions of first lumen 118.

Second inner wall surface 124 of first lumen 118 is positioned adjacent to and parallel to second inner wall surface 140 of second lumen 120. As such, first inner wall surface 128 of first lumen 118 is located on the side of first lumen 118 remote from second lumen 120. Second inner wall surfaces 124 and 140 also define opposite sides of a septum that longitudinally extends between proximal end 106 and distal end 108. As depicted in FIG. 8, septum 149 is further defined as having a transverse first side 151 extending between junctions 132 and 148 and a transverse second side 153 extending between junctions 138 and 154. Septum 149 also has a length extending between transverse first side wall 151 and transverse second side wall 153 that is equal to length $L_2$ of second inner wall surface 124. Furthermore, septum 149 has a width $W_1$ that extends between second inner wall surfaces 124 and 140.

Catheter body 122 is further defined as comprising a first body portion 155 that is substantially bounded on one side by exterior surface 104 of catheter 102 and on the opposing side by the combination of inner wall surfaces 126, 142, and first side 151 of septum 149. Catheter body 122 further comprises a second body portion 156 that is likewise bounded on one side by exterior surface 104 of catheter 102 and on the other side by the combination of inner side wall surface 130, 146, and second side 153 of septum 149.

A third body portion 158 of catheter body 122 is substantially bounded on one side by exterior surface 104 and on the opposing side by inner wall surface 128 of first lumen 118. Likewise, a fourth body portion 160 of catheter body 122 is bounded on opposing sides by exterior surface 104 and inner wall surface 144 of second lumen 120.

As previously mentioned, catheter 102 is attached to access port 50 in substantially the same way as catheter 46. More specifically, proximal end 106 of catheter 102 is advanced onto outlet stem 56 so that outlet prong 58 enters, for example, first lumen 118 while outlet prong 59 enters second lumen 120. Correspondingly, septum 149 is received between planar inner surface 62 of outlet prong 58 and planar inner surface 64 of outlet prong 59, substantially filling longitudinal slot 66. The width $W_1$ of septum 149 is dependent in part upon the variance between the length of second interior surface 124 and the width of inner surfaces 62 and 64 of outlet stem 56 and also between the length of second interior surface 139 and width of inner surface 64 of outlet stem 56. For example, when the width of inner surface 62 of outlet prong 58 is larger than the length $L_2$ of inner wall surface 124 of lumen 18, receiving outlet prong 58 within first lumen 118 forces septum 149 to stretch in length. As a result of septum 149 stretching, the width $W_1$ of septum 149 decreases. Accordingly, the width $W_1$ of septum 149 must be sufficiently large so that as septum 149 is stretched to receive outlet prong 58 within lumen 118 and outlet prong 59 within lumen 120, the resulting size of septum 149 is large enough to substantially fill longitudinal slot 66.

Unlike catheter 46, first lumen 118 and second lumen 120 do not have a shape complementary to the cross-sectional shape of outlet prongs 58 and 59. The elastomeric properties of the material of catheter 102, however, enables the lumens 118 and 120 to snugly receive outlet prongs 58 and 59. By sliding locking sleeve 60 over stem 56 having catheter 102 received thereon, a satisfactory mechanical and fluid coupling is thus effected between lumens 118 and 120 of catheter 102 and the fluid reservoirs within access port 50.

Figure 1:
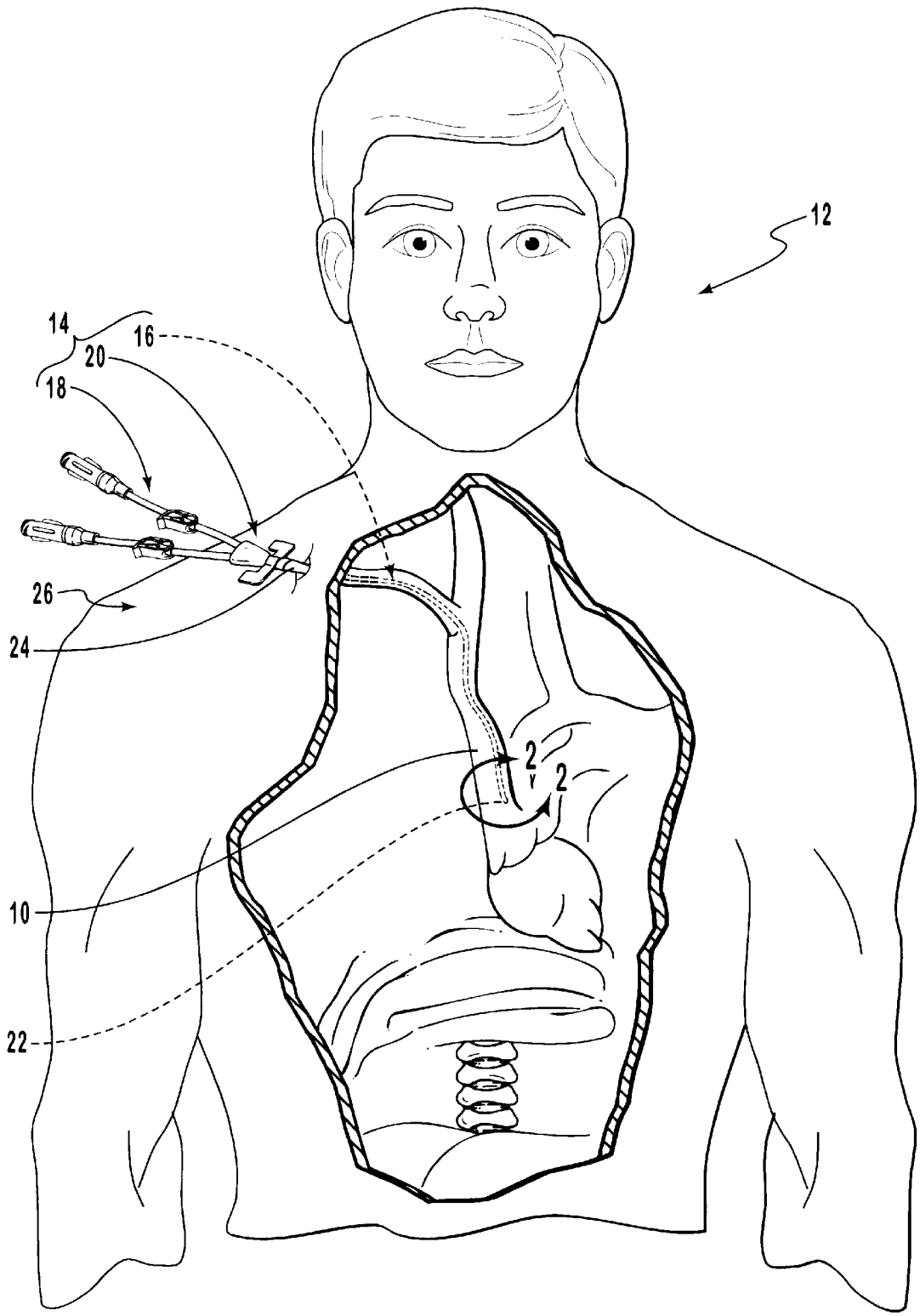
FIG. 1 is a perspective view of a vascular access system implanted in the body of a patient and affording direct external access to the proximal end of the dual lumen catheter of the implanted system.
Figure 2:
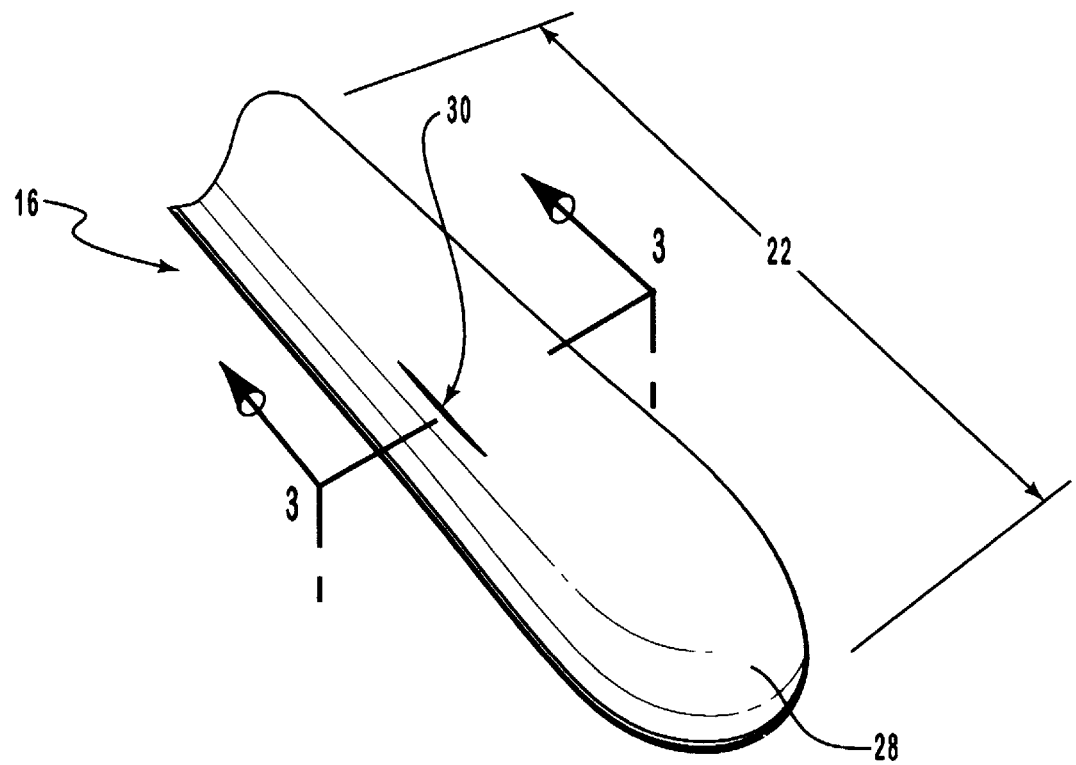
FIG. 2 is an enlarged perspective view of the distal end of the catheter of FIG. 1 showing a two-way, three-position valve thereat.
Figure 3:
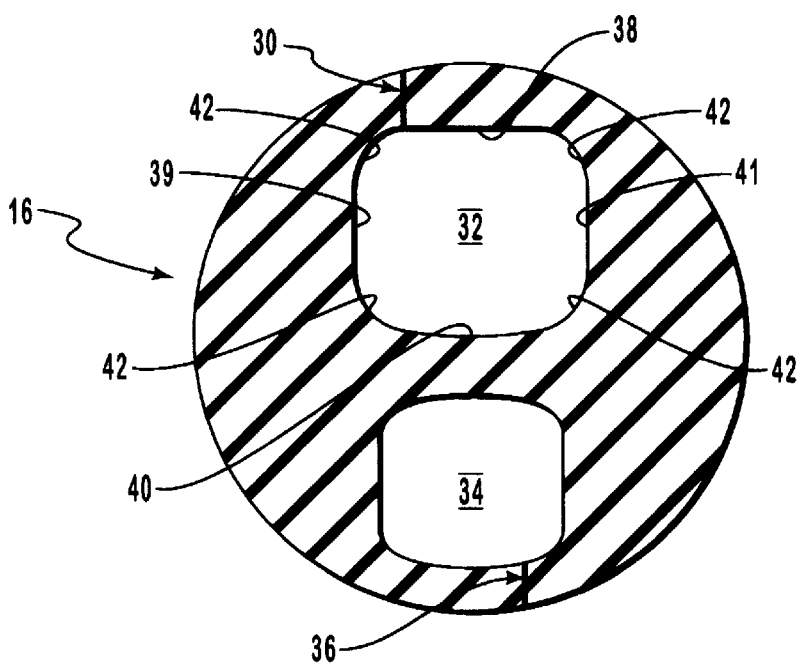
FIG. 3 is a transverse cross-sectional view of the catheter of FIG. 2 taken along section line 3—3 shown therein.
Figure 4:
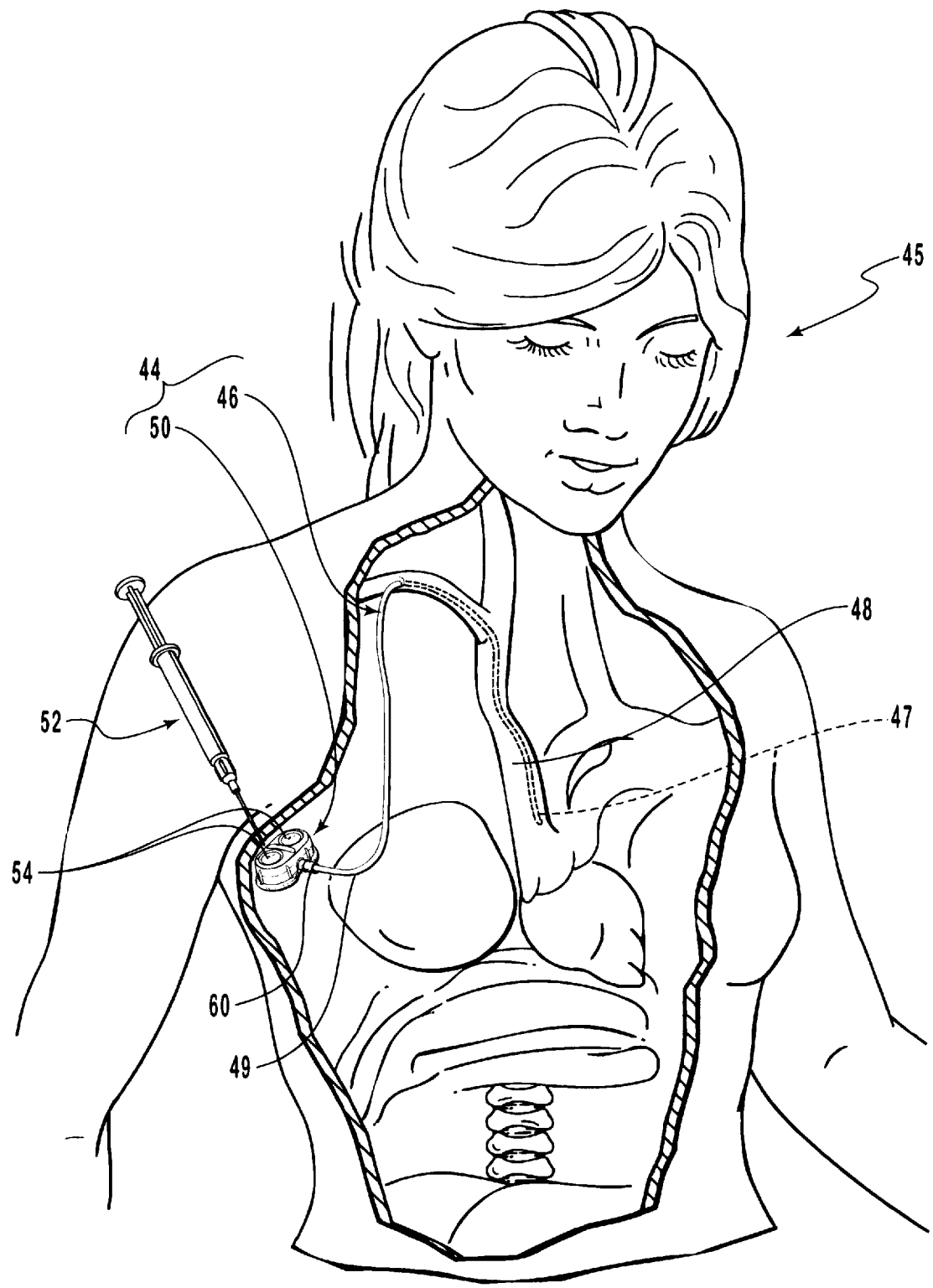
FIG. 4 is a perspective view of a second vascular access system implanted in the body of a patient and affording transcutaneous access with a hypodermic syringe to an implanted dual reservoir access port coupled to the proximal end of the dual lumen catheter of the implanted system.

As depicted in FIG. 8, lumen 118 and lumen 120 are both equally sized and symmetrically positioned on opposing sides of septum 149. This configuration has the advantage of allowing outlet prongs 58 and 59 of outlet stem 56 to be reversibly placed within either lumen 118 or 120. That is, lumen 118 can receive either outlet prong 58 or outlet prong 59 while lumen 120 receives the opposing prong. As a result, a medical practitioner does not have to worry about whether or not the proper prong is being received within the proper lumen. Furthermore, having lumens 118 and 120 of the same size eliminates having to monitor the position of the lumens. For example, lumen 34 of catheter 16 is smaller than lumen 32, as shown in FIG. 3. Where a medical practitioner is dispensing a highly viscous medicament, it can be vital that the medicament be dispersed within the larger of the lumens. As a result, it is necessary that the medical practitioner label or monitor the position of the different lumens. In contrast, since lumens 118 and 120 are of equal size, the medicament can be dispensed in either lumen without concern as to size.

Figure 9:
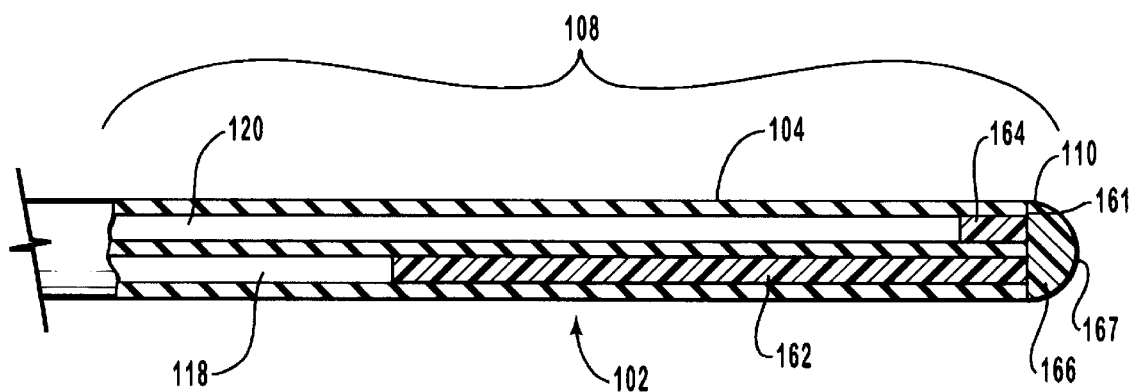
FIG. 9 is a longitudinal cross-section plan view of the distal end of the catheter of FIG. 7 taken along section line 9—9 shown therein and in FIG. 8.

FIG. 9 is a longitudinal cross-sectional plan view of distal end 108 of catheter 102 as taken along section line 9—9 shown in FIGS. 7 and 8. As disclosed therein, catheter 102 is initially formed with a distal end face 161. As better shown in FIG. 15, distal end face 161 defines an access 163 for first lumen 118 and an access 165 for second lumen 120. Referring again to FIG. 9, longitudinally disposed within first lumen 118 at distal end 108 is an elongated first plug 162. First plug 162 is formed so as to preclude fluid transfer between first lumen 118 at distal end face 161.

FIG. 9 also shows a second plug 164 disposed within second lumen 120 at distal end 108. Second plug 164 also precludes fluid transfer between second lumen 120 and distal end face 161. For reasons as will be discussed later, first plug 162 has a length greater than the length of second plug 164. As such, second lumen 120 extends closer to distal end face 161 than first lumen 118.

Formed at distal end face 161 so as to communicate with first plug 162 and second 164 is a semispherical head 166. Head 166 provides a smooth rounded exterior surface 167 that facilitates easy insertion and manipulation of catheter 102 within a body of a patient. The actual formation of first plug 162, second plug 164, and rounded head 166 will be discussed later.

Figure 10:
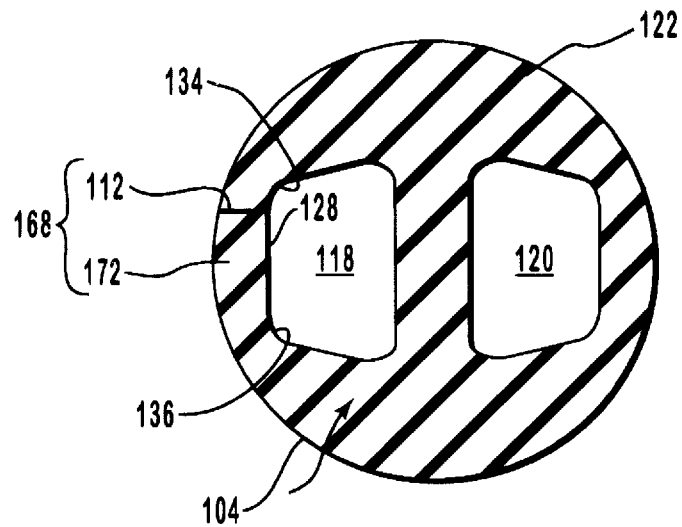
FIG. 10 is a transverse cross-sectional view of the catheter of FIG. 7 taken along section line 10—10 shown therein.

Referring now to FIG. 10, a transverse cross-sectional view of catheter 102 is shown taken along cross-section lines 10—10 as shown in FIG. 7. Disclosed therein is a first two-way, three-position valve 168 being biased into a closed position thereof in which fluid communication is precluded between first lumen 118 and exterior surface 104 of catheter 102. As will be discussed later with regard to FIGS. 12 through 14, valve 168 is selectively operable from said closed position thereof into either an inwardly or outwardly open position.

Valve 168 includes a slit 112 as previously disclosed with regard to FIG. 7. Slit 112 extends from exterior surface 104 to first lumen 118 at inner wall surface 128. Slit 112 is preferably positioned adjacent to junction 134 so as to asymmetrically intersect inner wall surface 128. Alternatively, slit 112 can be positioned adjacent to junction 136 or somewhere therebetween. Slit 112 is also positioned to intersect inner wall surface 128 at a right angle. As a result of slit 112 being positioned adjacent to junction 134, an operable valve wall 172 is formed of the section of third body portion 158 that extends from slit 112 to junction 136.

Figure 11:
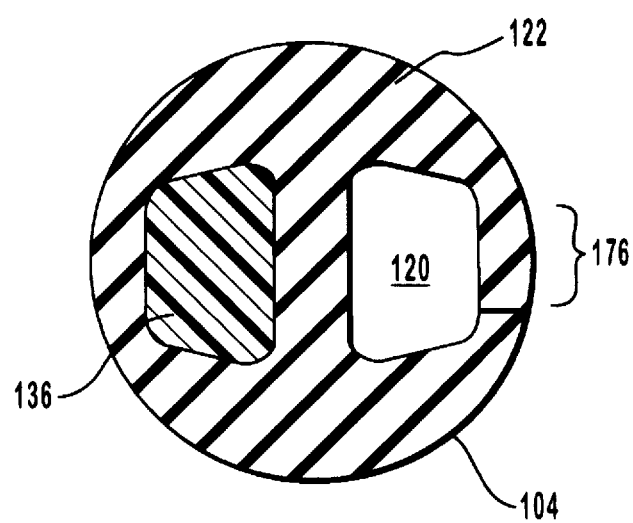
FIG. 11 is a transverse cross-sectional view of the catheter of FIG. 7 taken along section line 11—11 shown therein.

FIG. 11 is also a transverse cross-sectional view of catheter 102 but is taken along section line 11—11 of FIG. 7. As disclosed therein, a second two-way, three-position valve 176 is disclosed. As with first valve 168, second valve 176 is shown biased into a closed position thereof in which fluid communication is precluded between second lumen 120 and exterior surface 104. As discussed in greater detail in FIGS. 12–14, second valve 176 is selectively operable from said closed position thereof into either an inwardly or outwardly open position. FIG. 11 also shows first lumen 118 being blocked by first plug 162.

Figure 12:
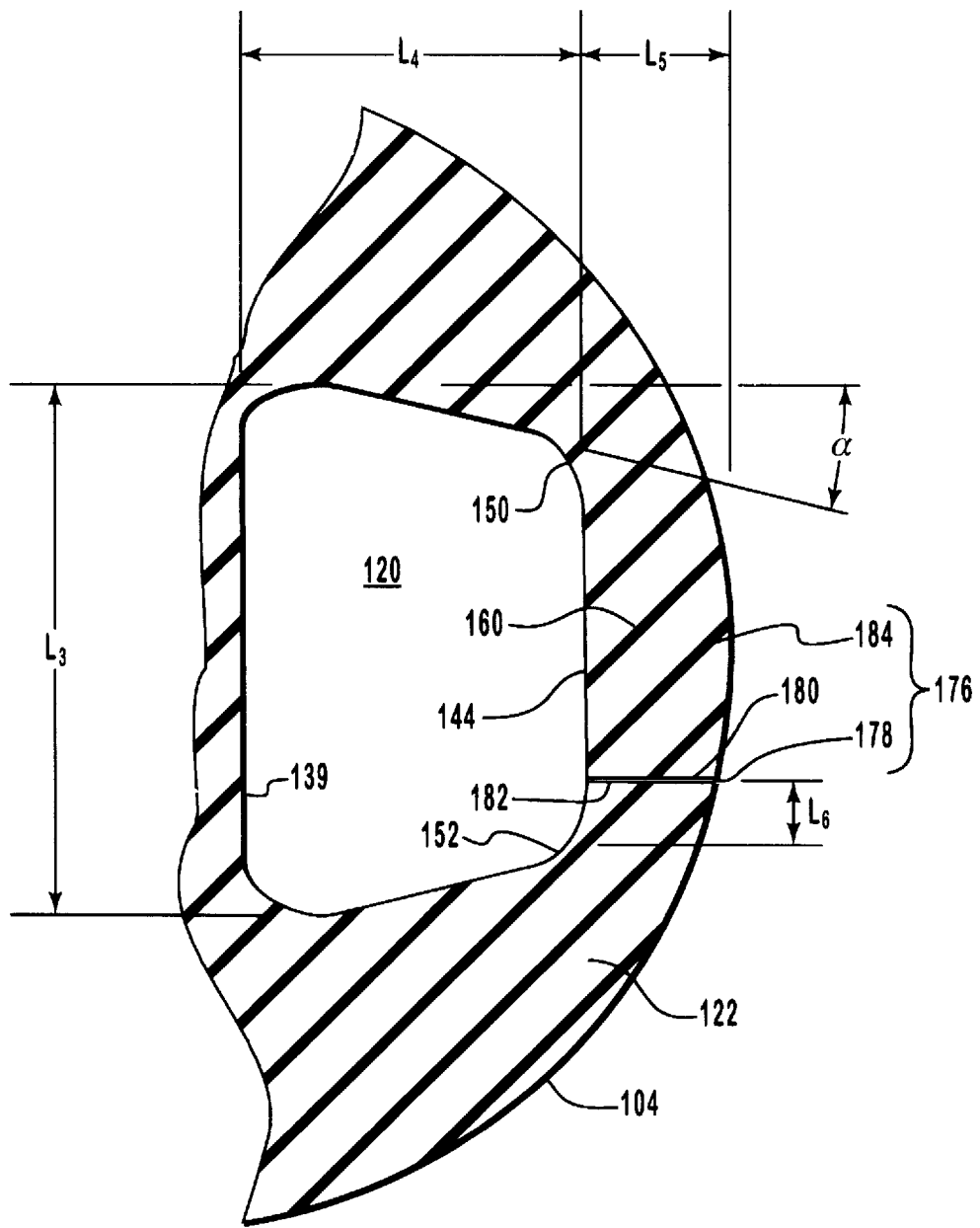
FIG. 12 is an enlarged cross-sectional view of a portion of the catheter of FIG. 11 illustrating in detail a two-way, three-position slit valve in the closed position thereof.

FIG. 12 is an enlarged view of second lumen 120 and second valve 176. Second valve 176 includes a slit 178 formed in catheter body 122 and extending from exterior surface 104 to second lumen 120. Slit 178 extends to second lumen 120 through sidewall 144 and is positioned so as to asymmetrically and perpendicularly intersect sidewall 144. Even though slit 178 is shown positioned adjacent to junction 152, slit 178 can also be positioned adjacent to junction 150 or disposed therebetween.

Slit 178 defines a first slit face 180 and an opposing second slit face 182. As depicted in FIG. 12, first slit face 180 and second slit face 182 sealingly engage each other so that second valve 176 is in a closed position. Second valve 176 is further shown as comprising an operative valve wall 184 which substantially comprises the section of fourth body portion 160 that extends from slit face 180 to junction 150.

Figure 13:
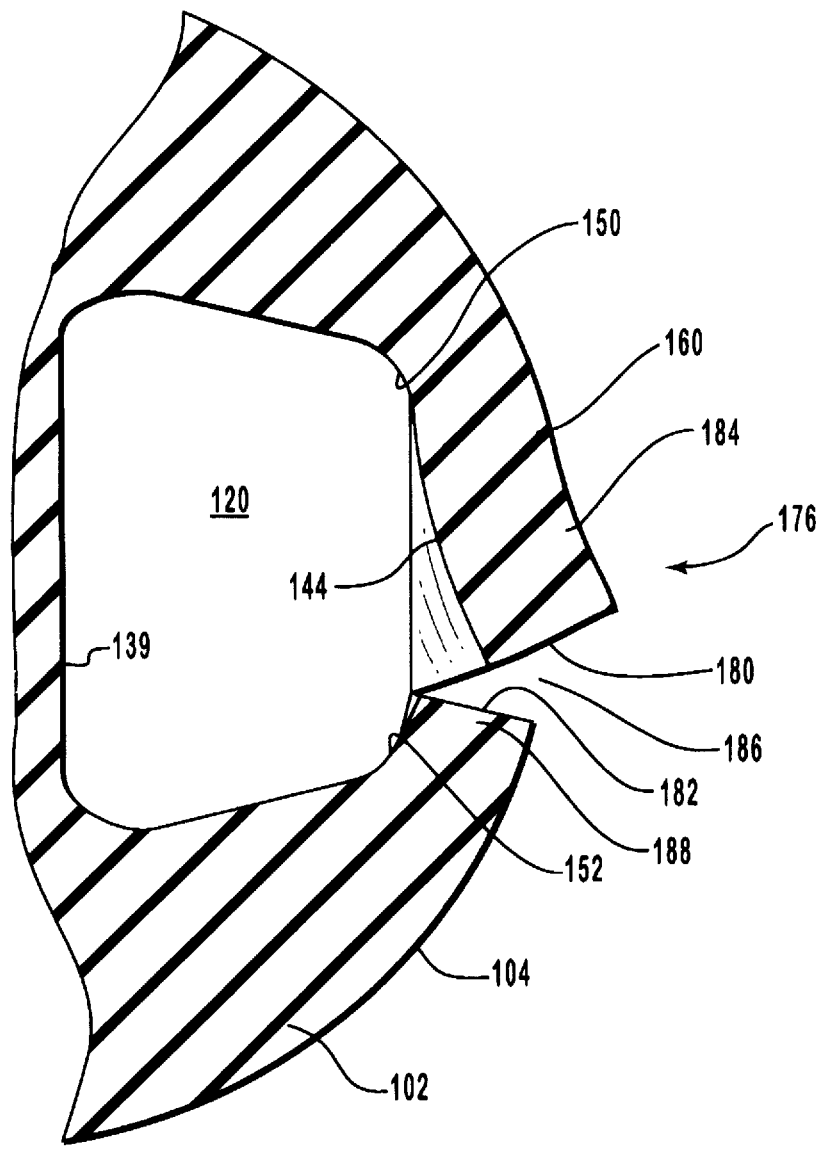
FIG. 13 is a cross-sectional view of the slit valve of FIG. 12 in the outwardly open position thereof.

Second valve 176 is depicted in FIG. 13 in an outwardly open position. As a fluid is injected within second lumen 120 from access port 50, the fluid causes a radially outward force on interior surface 139 of second lumen 120. The force resulting from the fluid causes valve wall 184 to radially flex outward. As a result, an opening 186 is formed between first slit face 180 and second slit face 182 through which fluid within lumen 120 can escape to exterior surface 104 of catheter 102. It is believed that valve wall 184 flexes at a uniform concentration extending from first slit face 180 to junction 150. This is in contrast to valve wall 184 simply hingedly rotating about junction 150.

FIG. 13 also discloses a section 188 of fourth body portion 160 adjacent to second slit face 182 flexing radially outward as fluid is dispersed through opening 186. As slit 178 is formed closer to junction 152, the flexing of section 188 decreases. Alternatively, when slit 178 is formed symmetrically between junctions 152 and 150, section 188 acts comparable to valve wall 184. That is, valve wall 184 and section 188 comparably flex inward and outward.

Figure 14:
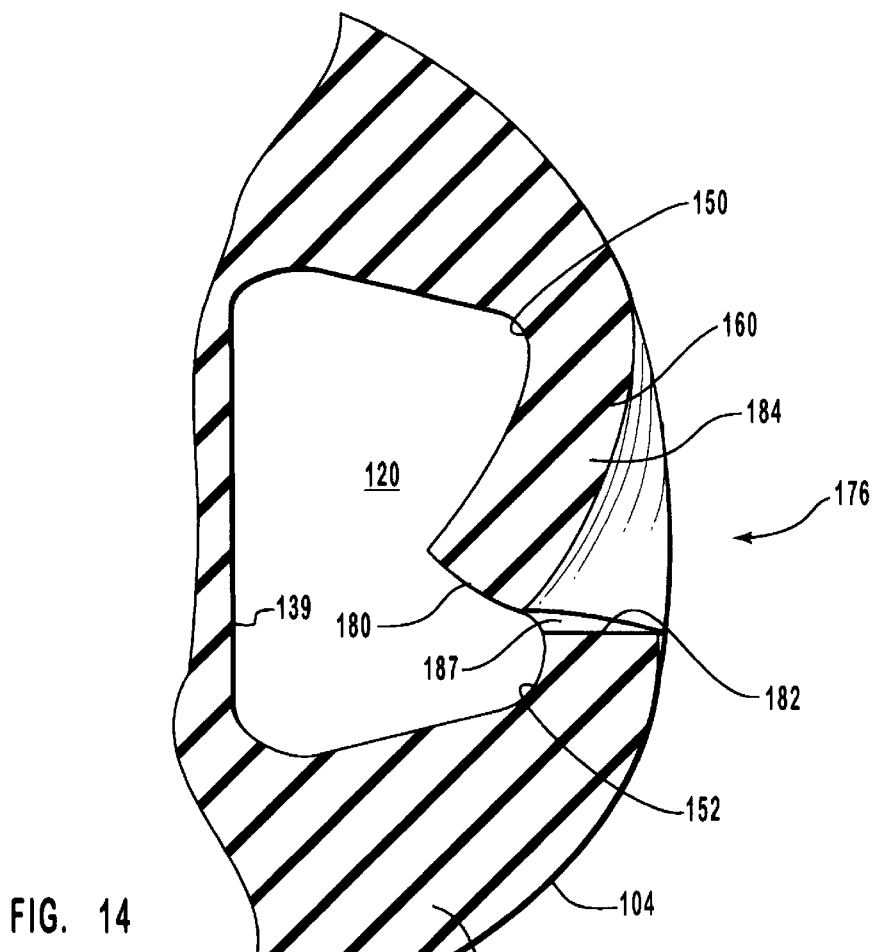
FIG. 14 is a cross-sectional view of the slit valve of FIG. 12 in the inwardly open position thereof.

Referring now to FIG. 14, by applying negative pressure, as measured relative to ambient atmospheric conditions, within lumen 120, such as when port 50 is used for aspiration, valve wall 184 radially flexes inward into the inwardly open position. As a result, an opening 187 is formed between first slit face 180 and second slit face 182. Opening 187 allows fluid from outside of catheter 102 to flow through opening 187 and into lumen 120. It is also believed that valve wall 184 flexes inwardly at a uniform concentration along the length of valve wall 184 extending from first slit face 180 and junction 150.

Catheter 102 is made from a resiliently flexible material. As a result, valve wall 184 automatically returns to the closed positioned wherein first slit face 180 and second slit face 182 are sealingly engaged when the positive or negative pressure on second lumen 120 is removed.

First valve 168 operates in a fashion identical to second valve 176. That is, as a positive pressure is applied to first lumen 118, valve wall 172 radially flexes outward to form an opening through which fluid can flow from first lumen 118 to the exterior of catheter 102. Likewise, as a negative pressure is applied to first lumen 118, valve wall 172 radially flexes inward to form an opening through which fluid from outside of catheter 102 can flow into first lumen 118.

It is evident by the comparisons between FIGS. 10 and 11 that first valve 168 and second valve 176 are longitudinally and radially offset from each other. That is, first valve 168 is positioned along section line 10—10 shown in FIG. 7, and second valve 176 is positioned distal of first valve 168 along section line 11—11. Although longitudinally displacing first valve 176 and second valve 168 is not necessary, several benefits are achieved. For example, slits 112 and 178 define relatively weak points on catheter 102 since they extend at least partially through catheter body 122. By longitudinally separating slits 112 and 178, the overall affect on the integrity of catheter 102 is minimized.

Furthermore, first lumen 118 and second lumen 120 can be used to serve different functions. For example, during a blood dialysis process, catheter 102 is received within a vein. Assuming first valve 168 is positioned upstream in the vein, first valve 168 would be used for aspiration while second valve 176, positioned down stream in the vein, would be used for fluid delivery. Having valves 168 and 176 horizontally adjacent to each other would diminish the functionality of catheter 102, since at least a portion of the fluid being delivered through second valve 176 would simultaneously be removed through first valve 168.

The present invention provides first valve means associated with first lumen 118 at distal end 116 of catheter body 122 (1) for selectively infusing fluid from first lumen 118 to exterior surface 104 of catheter body 122, (2) for selectively withdrawing fluid through first lumen 118 from exterior surface 104 of catheter body 122, and (3) for selectively precluding fluid communication between first lumen 122 and exterior surface 104 of catheter body 122. By way of example and not by limitation, first valve means includes first valve 168 including slit 112 and valve wall 172, as discussed above.

In an alternative embodiment, first valve means can comprise a pliable sleeve that is attached in fluid communication with first lumen 118. Formed on the pliable sleeve so as to be in fluid communication with first lumen 112 is a valve comparable to first valve 168. The pliable sleeve could have a closed end and be directly attached to distal end face 161. Alternatively, a hole could be formed extending from exterior surface 104 to first lumen 118. Catheter 102 could then be received within the pliable sleeve so that valve formed on the sleeve is positioned over the hole in catheter 102. In other embodiments, it is also envisioned that a plurality of valves such as first valve 168 could be formed on catheter body 122 in communication with first lumen 118.

The present invention also provides second valve means associated with second lumen 120 at distal end 108 of catheter body 122 (1) for selectively infusing a fluid from second lumen 120 to exterior surface 104 of catheter body 122, (2) for selectively withdrawing fluid through second lumen 120 from exterior surface 104 of catheter body 122, and (3) for selectively precluding fluid communication between second lumen 120 and exterior surface 104 of catheter body 122. By way of example and not by limitation, second valve means includes second valve 176 including slit 178 and valve wall 184 as discussed above. Second valve means further includes the same alternative embodiments as discussed above with regard to the first valve means.

Catheter 102 is preferably formed using conventional extruding processes. For most conventional purposes, catheter 102 is formed having a size in a range between about 3 French to about 12 French, with about 6 French to about 9 French being more preferred. As the size of catheter 102 increases the length L of slit 112 as shown in FIG. 7 also generally increases. By way of example, listed below are comparisons between catheter sizes and the corresponding preferred length L for slit 112:

| Catheter Size (French) | Slit Length Range (Inches) |
| --- | --- |
| 12 | 0.400–0.450 |
| 9 | 0.325–0.375 |
| 3 | 0.250–0.300 |

Although the above slit length ranges are discussed with regard to slit 112, it is also understood that slit 178 of second valve 176 would have a comparable length for a comparable catheter size.

Also outlined below are selected dimensions for one embodiment of a lumen of an inventive catheter such as lumen 120 of catheter 102. In each case, the dimensions are identified by corresponding reference characters shown in FIG. 12. The dimensions of the lumen are given in preferred tolerance ranges and are based on a catheter having a size of 7.5 French. Each of the dimensions are given in inches:

$L_3$=0.040–0.048
$L_4$=0.022–0.030
$L_5$=0.013–0.017
$L_6$=0.008–0.012

Lumen 120 is also shown as having an angle $\alpha$ in a range between about 13° to 17°.

The present invention also provides sealing means formed by the first set of inner wall surfaces of lumen 118 and the set of inner wall surfaces of lumen 120 at the proximal end 106 of catheter body 122. The sealing means is for affecting a fluid-tight mechanical engagement between outlet stem 56 of access port 50 and each of first lumen 118 and second lumen 120. By way of example and not by limitation, the sealing means includes the inner wall surfaces of lumen 118 and the inner wall surfaces of lumen 120 having a configuration and position as shown and discussed with regard to FIG. 8.

More specifically, as exemplified by lumen 118, first inner wall surface 128 is both linear and parallel to second inner wall surface 124 which is also linear. Furthermore, first inner wall surface 128 has a length that is shorter than the length of second inner wall surface 124. Accordingly, the formation of connection inner wall surfaces 126 and 130 results in lumen 118 having a substantially isosceles trapezoidal shape. As discussed with regard to FIG. 8, lumen 120 has a shape that is congruent with lumen 118.

Lumens 118 and 120 can also be modified to provide a variety of alternative sealing means. For example, whereas the inner wall surfaces of lumen 118 are connected by arcuate fillets, alternatively, straight sections or corners could be used in connecting the inner wall surfaces. In yet other embodiments, the connecting inner wall surfaces 126 and 130 of lumen 118 could be different sizes so that the trapezoidal shape of lumen 118 is not isosceles. In yet another alternative embodiment, first inner wall surface 128 need not be parallel to second inner wall surface 124. Likewise, the inner wall surfaces are not necessarily limited to having four (4) walls but can include five (5), six (6), seven (7) or even more linear inner wall surfaces. In some embodiments, it can even be envisioned that one of the inner wall surfaces may not be linear. Many of the above discussed alternative embodiments for the sealing means will be discussed later in greater detail.

Figure 15:
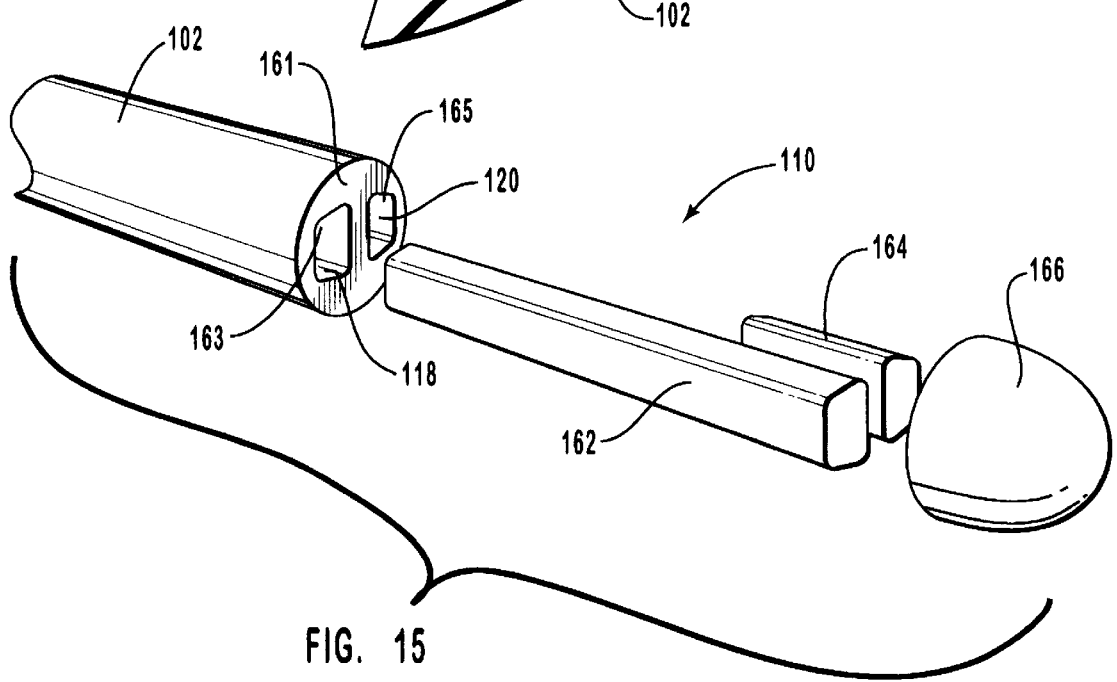
FIG. 15 is an exploded perspective view of the components of the distal tip of the catheter of FIG. 7.

FIG. 15 is an exploded perspective view of the components of distal tip 110 of catheter 102. As shown therein, distal tip 110 includes first plug 162 removed from first lumen 118; second plug 164 removed from second lumen 120; and head 166 separated from distal end face 161.

Figure 16A:
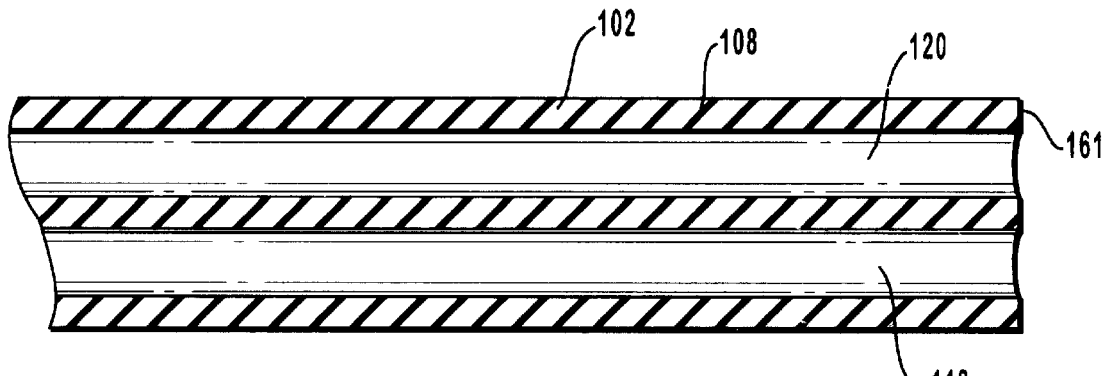
FIGS. 16A–16G are longitudinal cross-sectional plan views, similar to that of FIG. 9, showing in sequence steps in the manufacture of the distal end of the catheter of FIG. 7.
Figure 16B:
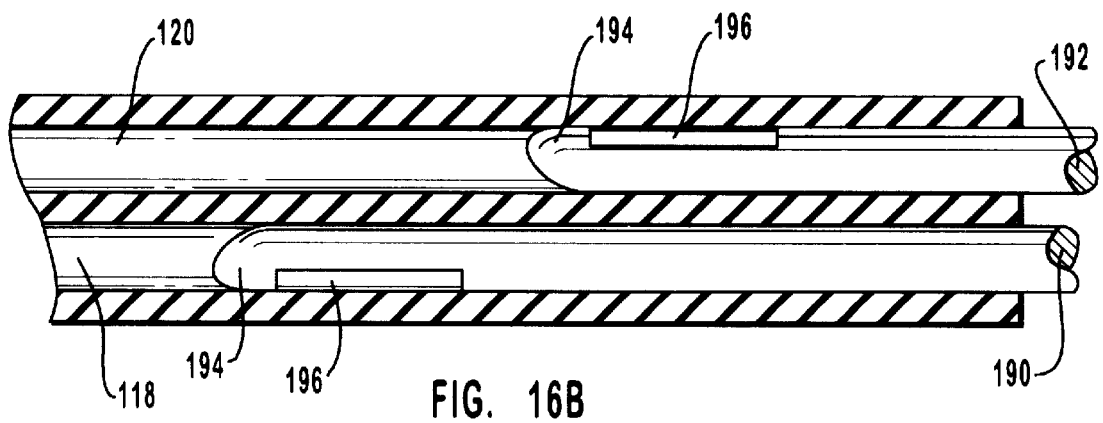

FIGS. 16A through 16G disclose a series of depictions of the manufacturing process used in forming distal tip 110. FIG. 16A is a longitudinal cross-sectional view of distal end 108 of catheter 102 prior to formation of distal tip 110. As shown therein, first lumen 118 and second lumen 120 openly extend to distal end face 161. In the initial stage of manufacture as depicted in FIG. 16B, mandrels 190 and 192 are received within first lumen 118 and second lumen 120, respectively. Each of mandrel 190 and mandrel 192 has a rounded insert end 194 and an elongated receiving slot 196 longitudinally formed therein near insert end 194.

Figure 16C:
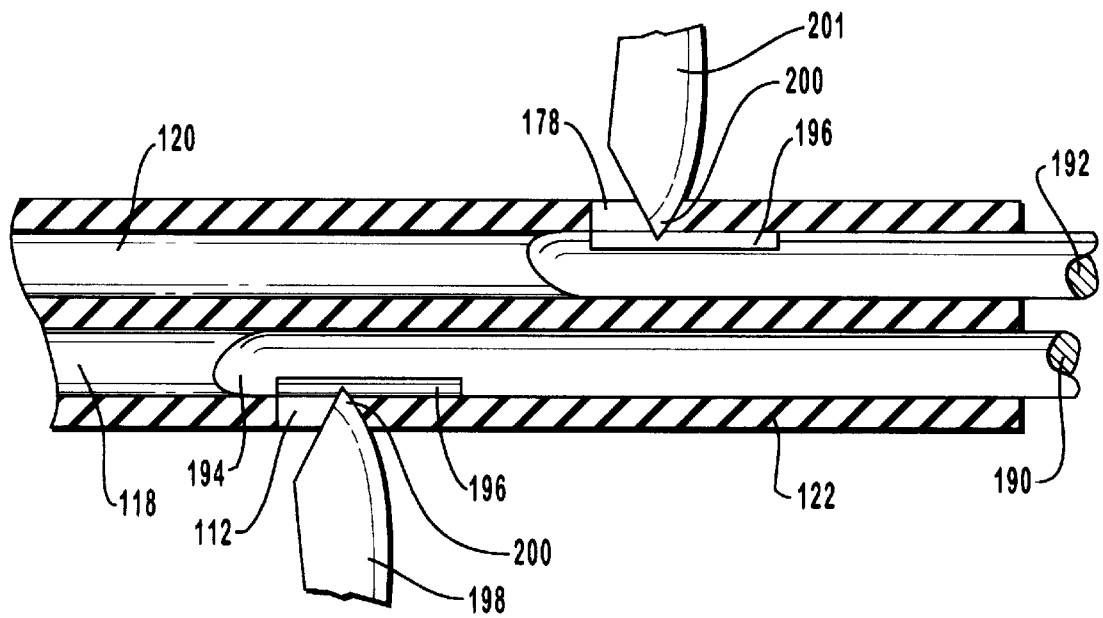

As depicted in FIG. 16C, a knife blade 198 having a point 200 penetrates through catheter body 122 and into receiving slot 196 of mandrel 190. Knife blade 198 is then advanced along the longitudinal axis of catheter body 122 to form slit 112. Slot 196 enables knife blade 198 to cut through catheter body 122 without having to contact mandrel 190 and thus potentially dull knife blade 198.

In like manner, a knife blade 201 also having a point 200 is used to penetrate through catheter body 122 into slot 196 to cut slit 178. It is noted that FIG. 16C is only a depiction of the process of forming slits 112 and 178. In the preferred embodiment, as shown in FIG. 7, slits 112 and 178 are not positioned on the same cross-sectional plane and thus would not be simultaneously shown as depicted in FIG. 16C.

Figure 16D:
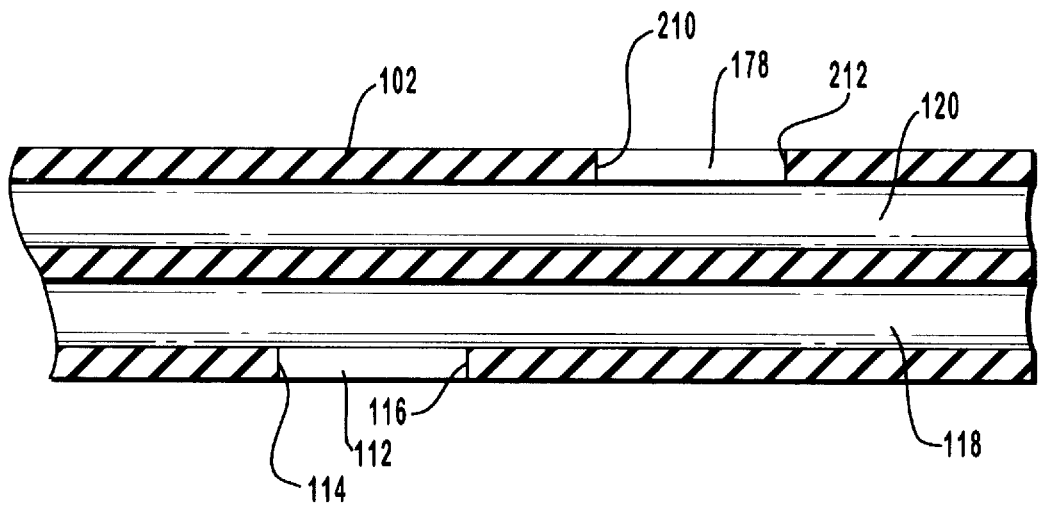

FIG. 16D discloses catheter 102 having slits 112 and 178 formed therein and mandrels 190 and 192 removed therefrom. Slit 112 extends between proximal end 114 and distal end 116 as discussed with regard to FIG. 7. Likewise, slit 178 also extends between a proximal end 210 and a distal end 212.

Figure 16E:
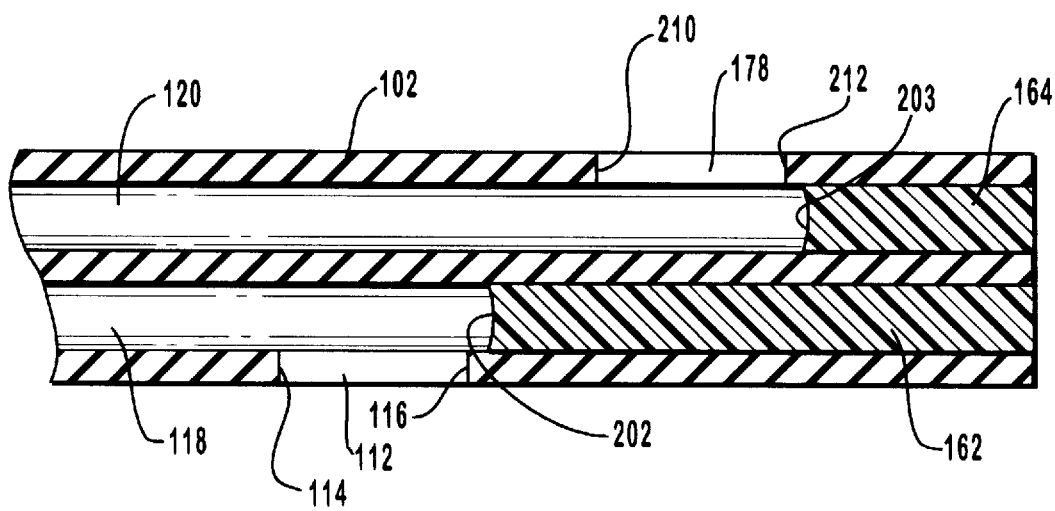

In the next step of the manufacturing process, as shown in FIG. 16E, first plug 162 is formed by injecting a liquid plugging material within first lumen 118 until a proximal end 202 of first plug 162 is positioned adjacent to distal end 114 of slit 112. The preferred plugging material is a liquid silicone rubber doped with a tungsten powder. One embodiment of a liquid silicone rubber can be purchased from Dow Corning under the name Silastic®. In alternative embodiments, other biocompatible adhesives can be used.

Proximal end 202 of first plug 162 is preferably within about twelve thousandth of an inch of distal end 114 of slit 112. First plug 162 thus serves the function of preventing blood or other fluids from freely flowing into first lumen 118 when catheter 102 is implanted within a body. Furthermore, as a result of first plug 162 being positioned adjacent to slit 112, first plug 162 prevents fluids delivered into first lumen 118 from access port 50 from pooling and potentially stagnating distal of slit 112.

Using the same process, second plug 164 is formed by injecting a plugging material within second lumen 120 so that a proximal end 203 of second plug 164 is positioned at or slightly distal of distal end 212 of slit 178. Second plug 164 performs the same function with regard to second lumen 120 as first plug 162 performs with regard to first lumen 118.

Figure 16F:
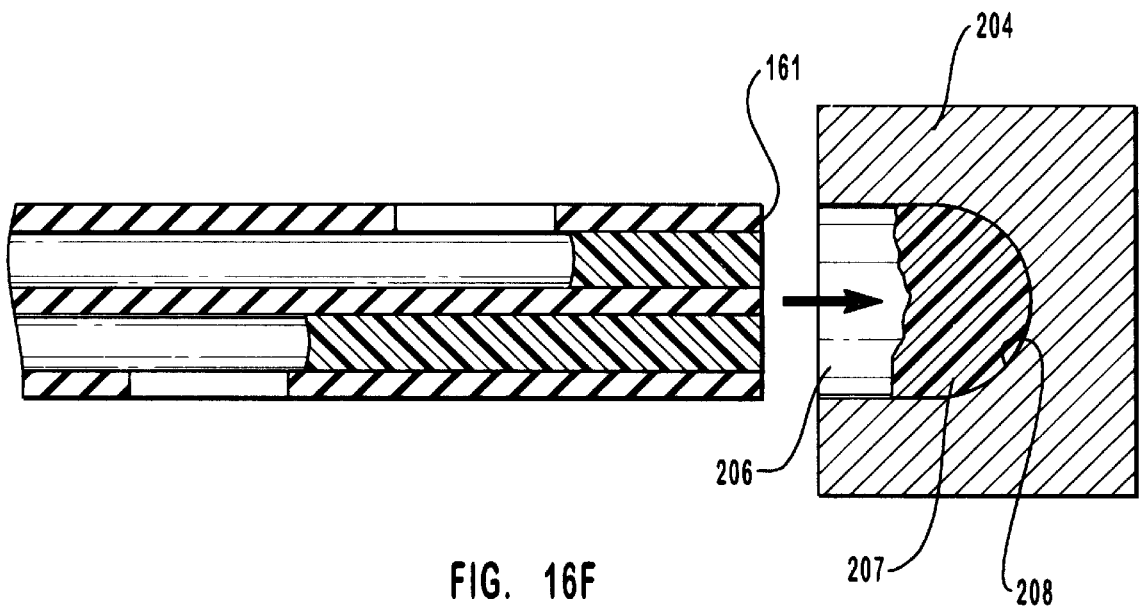

Referring to FIG. 16F, a mold 204 is shown having a receiving cavity 206. Receiving cavity 206 has a hemispherical portion 208 that is likewise filled with a plugging material 207.

Figure 16G:
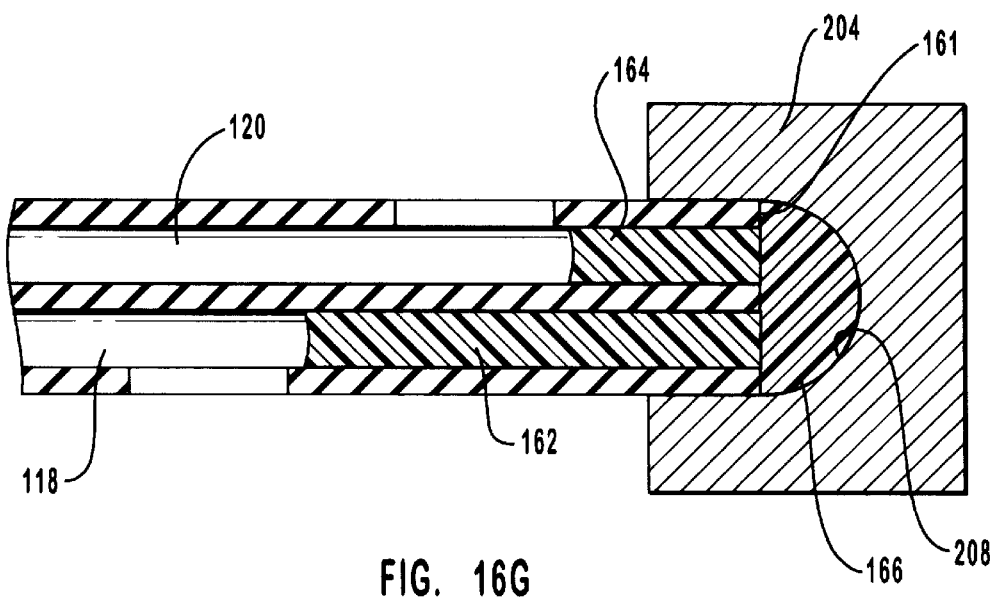

As next shown in FIG. 16G, distal end face 161 of catheter 102 is received within cavity 206 so that distal end face 161 is biased against plugging material 207 within hemispherical portion 208. As a result, head 166 is formed on distal end face 161. In this configuration, the plugging material constituting the first plug 162, second plug 164, and head 166 is allowed to harden either under ambient conditions or increased heat. Once the plugging material has hardened, mold 204 is removed.

Although unnecessary, in one embodiment distal end 110 of catheter 102 can be soaked in a silicone oil such as fluoro silicone which can be purchased from Dow Corning. The silicone oil softens and thereby increases the flexibility of the silicone material comprising catheter 102. The softening of the silicone material has been found to increase the effectiveness of a two-way, three-position valve, such as first valve 168, when formed on a single inner catheter. To optimize the effectiveness of the valves with regard to a single lumen catheter, the portion of the catheter with the valve is soaked in the silicone oil for a period in a range between about 12 hours to about 24 hours.

One of the advantages of catheter 102 over conventional D-shaped catheters, such as catheter 46, is increased kink resistance. As used herein, kink resistance refers to the ability of a catheter to bend without closing off fluid flow through the lumens. Kink resistance of catheter 102 is greater than a conventional D-shaped catheter as a result of an increase in the area moment of inertia, which corresponds to an increase in the resistance to bending, and the structural body 122 to withstand increased compressive forces without failure.

Figures 17A, 17B:
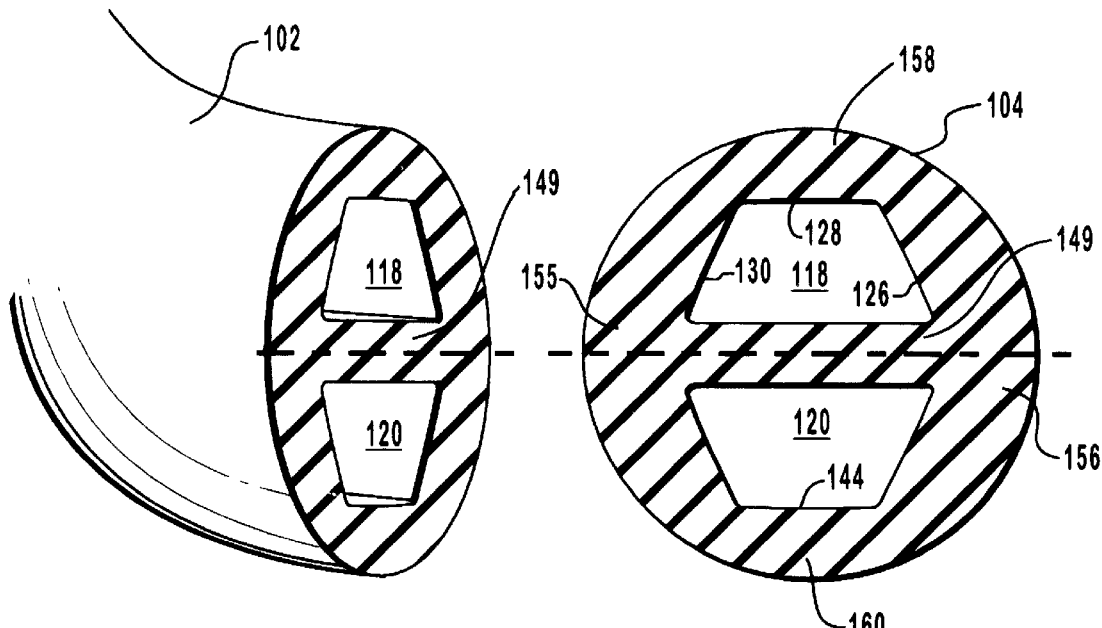
FIG. 17A is a perspective view in partial cross section of the catheter of FIG. 7 being bent in a plane perpendicular to the plane of the septum thereof.
FIG. 17B is a transverse cross-sectional view of the catheter of FIG. 17A by which to illustrate the bending stresses arising therein.

For example, turning to FIG. 17A, catheter 102 is shown as bending perpendicular to the longitudinal transverse axis of septum 149. Catheters are generally weakest along this axis since there is minimal material to resist kinking. As shown in FIG. 17B, however, as a result of lumen 118 having linear inner wall surface 128 adjacent to exterior surface 104, third body portion 158 of catheter body 122 has a relatively large material area compared to the corresponding area on a D-shaped lumens. This is because D-shaped lumens have a curved surface that is equally spaced from the exterior surface of the catheter.

As a result of the large material area of the third body portion 158 and the opposing fourth body portion 160, the area moment of inertia of catheter 102 is increased when taken about the longitudinal transverse axis of stem 149. Furthermore, as a result of side wall surface 126 and 130 being linear rather than curved, first body portion 155 and second body portion 156 are able to withstand higher compressive forces caused by the bending of catheter 102 before kinking. Accordingly, although catheter 102 is still easily bent for its intended use, the combination of the increased area moment of inertia and structural resistance to compression results in an overall increase in the kink resistance.

Figures 18A, 18B:
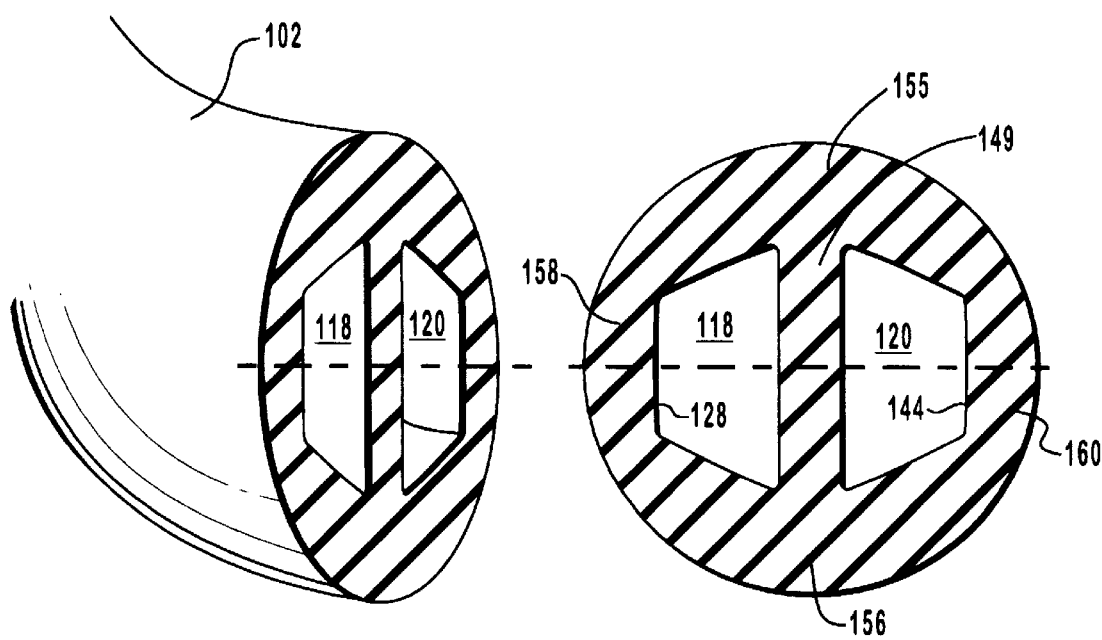
FIG. 18A is a perspective view in partial cross section of the catheter of FIG. 7 bent in the plane of the septum thereof.
FIG. 18B is a transverse cross-sectional view of the catheter of FIG. 18A by which to illustrate the bending stresses arising therein.
Figures 19, 20, 21:
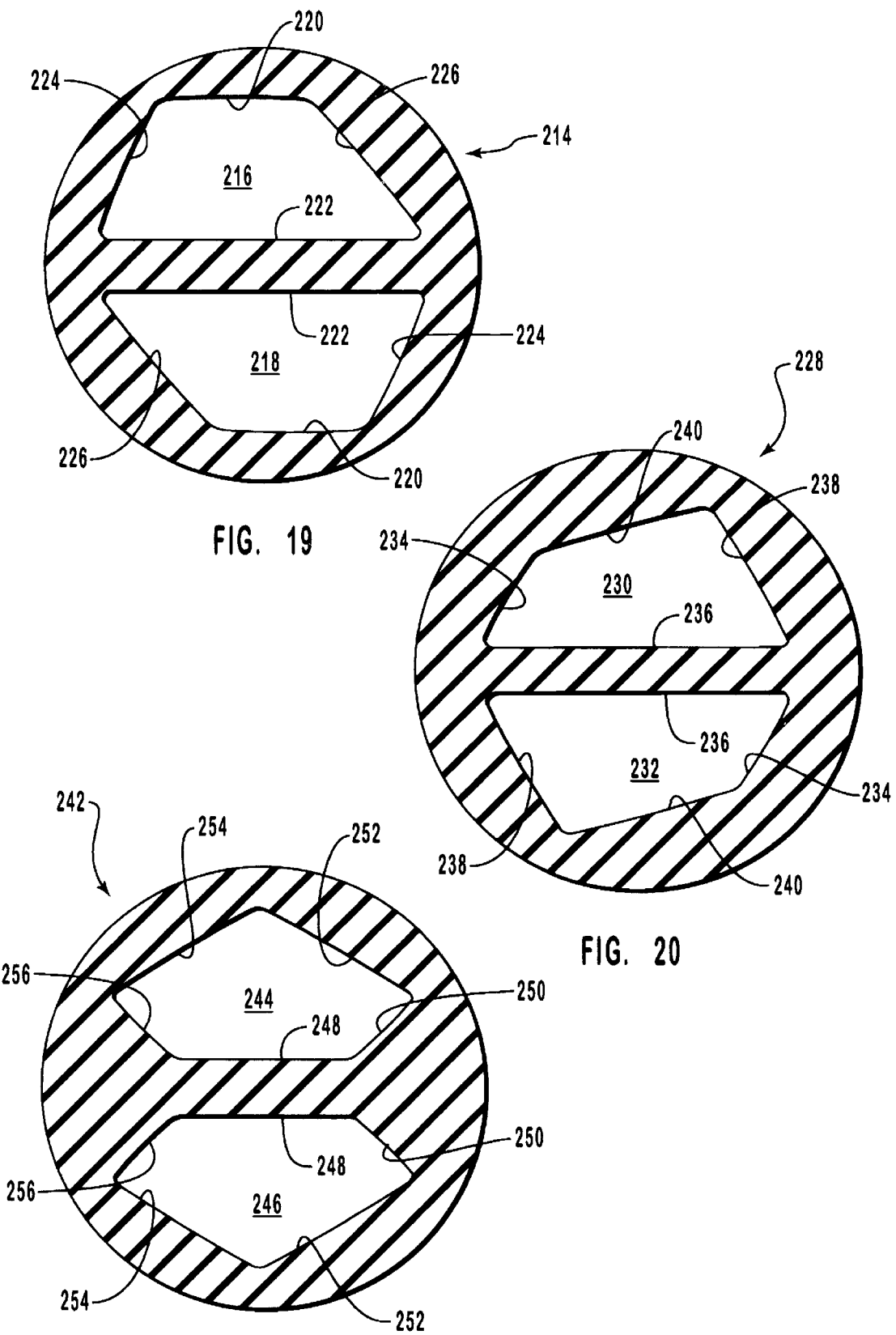
FIG. 19 is a transverse cross-sectional view of a second embodiment of a dual lumen catheter incorporating teachings of the present invention.
FIG. 20 is a transverse cross-sectional view of a third embodiment of a dual lumen catheter incorporating teachings of the present invention.
FIG. 21 is a transverse cross-sectional view of a fourth embodiment of a dual lumen catheter incorporating teachings of the present invention.

FIGS. 18A and B show catheter 102 bending parallel to the transverse longitudinal access of septum 149. In this configuration, the presence of septum 149 in conjunction with first portion 155 and second portion 156 of catheter body 122 form a large I-beam which increases the area moment of inertia about the corresponding axis. Furthermore, the fact that side wall surfaces 128 and 144 are linear rather then curved enables third body portion 158 and fourth body portion 160 to withstand higher compressive forces caused by the bending of catheter 102 before kinking FIG. 19 is a transverse cross-sectional view of a second embodiment of a dual lumen catheter 214 incorporating teachings of the present invention. Catheter 214 is shown as having a first lumen 216 and an adjacent second lumen 218. Each of lumens 216 and 218 have a first inner side wall 220 and an opposing second inner side wall 222 comparable to corresponding side wall surfaces on first lumen 118 and second lumen 120 of FIG. 8. Lumens 216 and 218 of FIG. 19 are distinguished from lumens 118 and 120 of FIG. 18 in that lumens 216 and 218 each include connecting side wall surfaces 224 and 226 which are of unequal length. As such the trapezoidal shapes of lumens 216 and 218 are not isosceles.

Nevertheless, as a result of the linear configuration of the inner wall surfaces and the similarity in structure between lumens 216 and 218, catheter 214 can be connected to access port 50 and incorporate a two way three-position valve with each of lumens 216 and 218.

FIG. 20 is a transverse cross-sectional view of yet a third embodiment of a dual lumen catheter 228 also incorporating teachings of the present invention. Catheter 228 includes a first lumen 230 and an adjacent second lumen 232. Each of lumens 230 and 232 are defined by a series of four linear inner wall surfaces 234, 236, 238, and 240. Unlike catheter 214 in FIG. 19 and catheter 102 in FIG. 7, none of the inner wall surfaces within each of discreet lumens 230 and 232 are parallel.

Furthermore, at least one of the inner wall surfaces has a length that is smaller than a second of the inner wall surfaces. For example, inner wall surface 234 is smaller than inner wall surface 240. Catheter 228 can also be used for attachment to a dual reservoir access port such as access port 50 and can accommodate a two-way, three-position valve with each of lumens 230 and 232.

FIG. 21 is a transverse cross-sectional view of a fourth embodiment of a dual lumen catheter 242 incorporating teachings of the present invention. Catheter 242 includes a first lumen 244 and an adjacent second lumen 246. Each of lumens 244 and 246 are defined by five linear inner wall surfaces 248, 250, 252, 254, and 256. As with catheter 228 in FIG. 20, each of lumens 244 and 246 have a first inner wall surface that is shorter than a second inner wall surface. For example, inner wall surface 256 is shorter than inner wall surface 248.

As with catheters 228 and 214, catheter 242 has improved kink resistance as a result of the structure of the lumens 244 and 246 and can be attached to a dual reservoir port such as access port 50. Furthermore, a two-way, three-position valve can be associated with each of lumens 244 and 246. For example, a slit can be formed in either of inner wall surfaces 254 or 252 of lumen 246 for formation of a two-way, three-position valve.

It is also noted that for the same reasons that each of the above discussed invented catheters have improved kink resistance, the inventive catheters also have an increased resistance to collapse. Collapsing typically occurs when a negative pressure applied to a select lumen causes the inner wall surfaces of the lumen to collapse, thereby constricting or completely blocking flow of fluid through the lumen.

Figure 22:
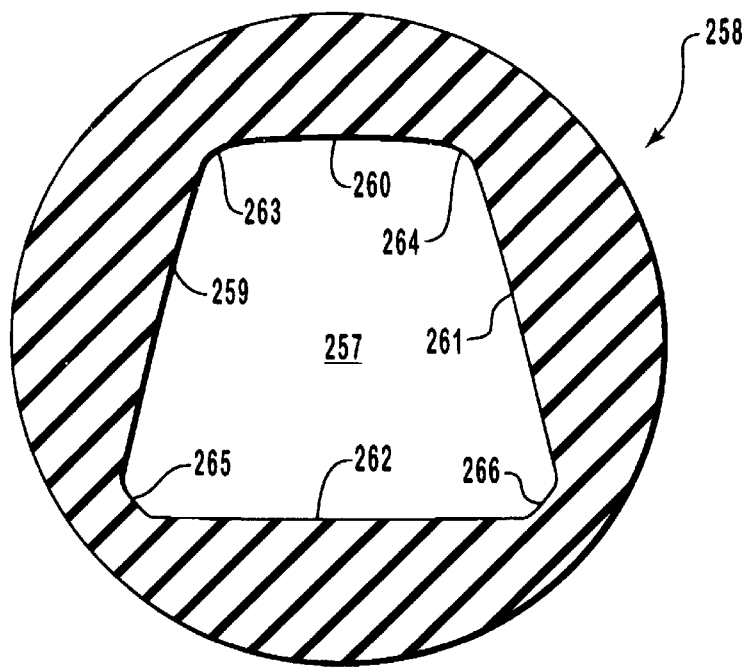
FIG. 22 is a transverse cross-sectional view of a first embodiment of a single lumen catheter incorporating teachings of the present invention.

FIG. 22 is a transverse cross-sectional view of a first embodiment of a single lumen catheter 258 incorporating teachings of the present invention. Catheter 258 has four inner side wall surfaces that define a lumen 257 having an isosceles trapezoidal shape comparable to first lumen 118 of catheter 102. Wall surfaces 259 and 260 are connected by junction 263, and wall surfaces 261 and 260 are connected by junction 264. Junction 263 and junction 264 are shown as arcuate fillets. In contrast, wall surfaces 259 and 262 are connected by a straight section 265, and wall surfaces 261 and 262 are connected by straight section 266.

As a result of lumen 257 being comparable to lumen 118, catheter 258 can be attached to a singe reservoir port and either have an open end or have a two-way three position valve associated therewith. Furthermore, as a result of the shape of lumen 257, catheter 258 has increased kink resistance.

Figure 23:
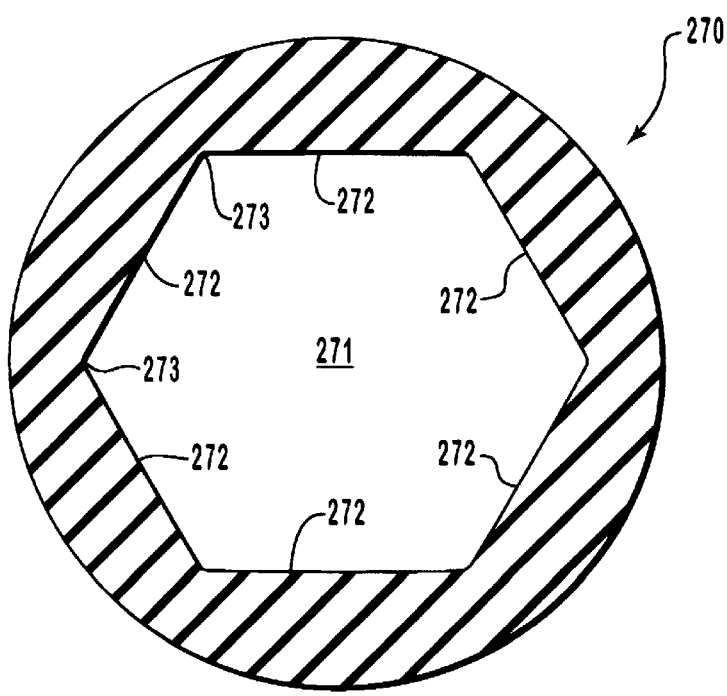
FIG. 23 is a transverse cross-sectional view of a second embodiment of a single lumen catheter incorporating teachings of the present invention.

FIG. 23 is a transverse cross-sectional view of a second embodiment of a single lumen catheter 270 incorporating teachings of the present invention. Catheter 270 has a lumen 271 defined by six inner sidewall surfaces 272 each having equal length and being joined at junctions 273. Catheter 270 can also be attached to a singe reservoir port and either have an open end or have a two-way three position valve associated therewith. Furthermore, as a result of the linear sidewall surfaces, catheter 270 also has increased kink resistance.

Figure 24:
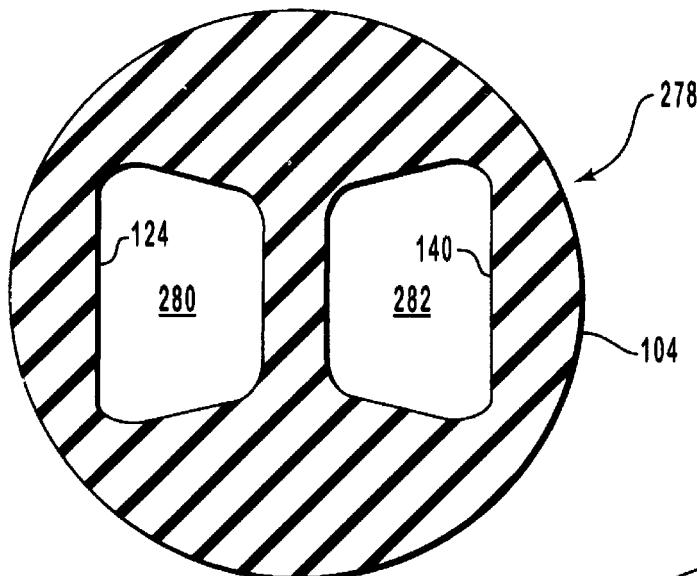
FIG. 24 is a transverse cross-sectional view of a fifth embodiment of a dual lumen catheter incorporating teachings of the present invention.

FIG. 24 is a transverse cross-sectional view of a fifth embodiment of a dual lumen catheter 278 incorporating teachings of the present invention. Catheter 278 includes a first lumen 280 and a second lumen 282 that are each defined by a plurality of linear inner wall surfaces as previously discussed with first catheter 118 and second catheter 120. The distinction between catheter 278 and catheter 102 is that lumens 280 and 282 have been rotated 180° relative to lumens 118 and 120. Accordingly, second inner wall surfaces 124 and 140 are now positioned adjacent to exterior surface 104. Attachment of catheter 278 to a dual reservoir access port may require the port to have a modified stem configuration as compared to access port 50. Catheter 278 still enables, however, the association of a two-way, three-position valve. That is, a two-way, three positioned valve such as first valve 168 could be formed so as to interact with either of interior wall surfaces 124 or 140.

Figure 25:
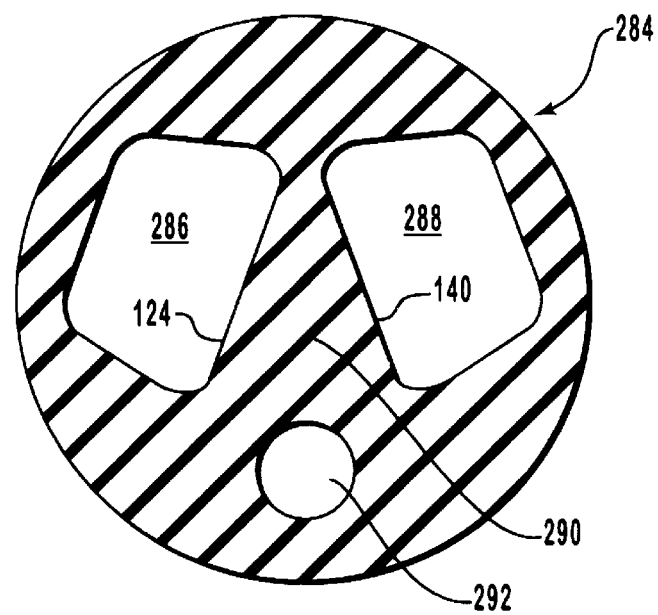
FIG. 25 is a transverse cross-sectional view of a catheter having a small circular lumen and incorporating teachings of the present invention.

FIG. 25 is a transverse cross-sectional view of a first embodiment of a triple lumen catheter 284 incorporating teachings of the present invention. Catheter 284 includes a first lumen 286 and an adjacent second lumen 288. As viewed in FIG. 25, lumens 286 and 288 are comparable to and have the same inner wall surfaces as first lumen 118 and second lumen 120, respectively of catheter 102.

Catheter 284 is distinguished from catheter 102 in that second inner wall surface of lumen 286 is no longer parallel to second inner wall surface 140 of lumen 228. As a result, a wedged-shaped septum 290 is formed between inner wall surfaces 124 and 140. Catheter 284 further includes a circular lumen 292 that longitudinally extends the length of catheter 284. In one embodiment, lumen 292 can be used to receive a guidewire for placement of catheter 284.

It is envisioned that catheter 284 could be attached in a mechanical fluid-tight connection to a stem of a dual reservoir port that has been modified to have a comparable configuration as lumens 286 and 288 of catheter 284. As with the other catheters having trapezoidal-shaped lumens, catheter 284 also has a benefit of improved kink resistance and the selective incorporation of two-way, three-position valve so as to communicate with either of lumens 286 and 288.

Figure 26:
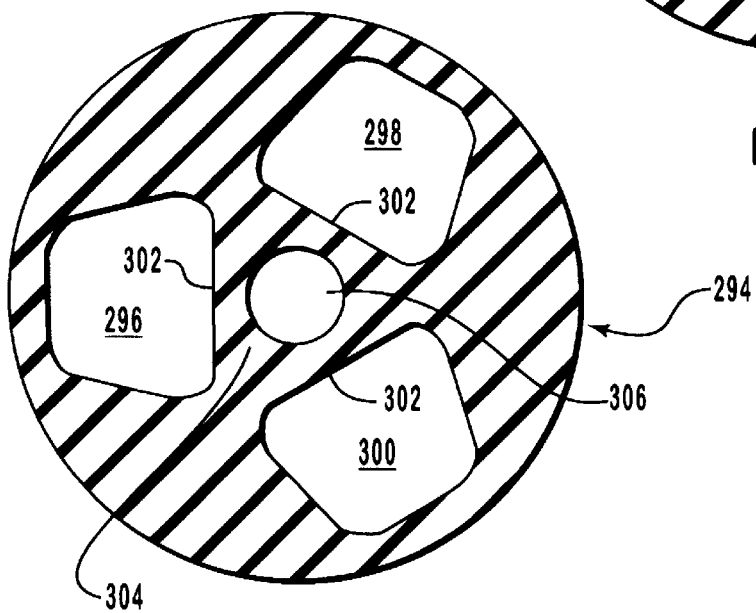
FIG. 26 is a transverse cross-sectional view of a second embodiment of a catheter having a small circular lumen and incorporating teachings of the present invention.

Finally, FIG. 26 is a transverse cross-sectional view of a first embodiment of a quadruple lumen catheter 294 incorporating teaches of the present invention. Catheter 294 includes three (3) substantially trapezoidal-shaped lumens 296, 298 and 300 each having a second inner wall surface 302 adjacent to the longitudinal access of catheter 294. Lumens 296, 298 and 300 each have a shape comparable to first lumen 118. Furthermore, lumens 296, 298 and 300 are symmetrically formed within catheter 298 so that inner wall surfaces 302 form a substantially triangular septum 304.

Longitudinally extending through septum 304 is a circular lumen 306. As with lumen 292 of catheter 284, lumen 306 can also be used to receive a guidewire for insertion of catheter 294. It is likewise envisioned that once catheter 294 is received within a body, catheter 294 can be attached to a triple reservoir port having a stem configuration comparable to the configuration of lumens 296, 298 and 300. Furthermore, catheter 294 has the advantages of having trapezoidal-shaped lumens which increase kink resistance and facilitate the incorporation of two-way, three-position valves.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dual lumen catheter implantable in the body of a patient, said catheter comprising:

(a) an elongated catheter body of elastomeric material having a longitudinal axis, an exterior surface, a distal end, and an open proximal end;

(b) a first lumen longitudinally extending through said catheter body from said proximal end to said distal end thereof and being defined by a first set of longitudinally extending inner wall surfaces, the cross section of said first lumen in a transverse cross section of said catheter body taken normal to said longitudinal axis thereof comprising:

(i) a generally linear first inner wall surface of said first set of inner wall surfaces; and (ii) a generally linear second inner wall surface of said first set of inner wall surfaces, said second inner wall surface being nonadjacent to said first inner wall surface, and the length of said first inner wall surface of said first set of inner wall surfaces being less than the length of said second inner wall surface of said first set of inner wall surfaces;

(c) a second lumen longitudinally extending through said catheter body from said proximal end to said distal end thereof and being defined by a second set of longitudinally extending inner wall surfaces; and (d) first valve means associated with said first lumen at said distal end of said catheter body (1) for selectively infusing fluid from said first lumen to said exterior of said catheter body, (2) for selectively withdrawing fluid through said first lumen from said exterior of said catheter body, and (3) for selectively precluding fluid communication between said first lumen and said exterior of said catheter body.

2. A dual lumen catheter as recited in claim 1, wherein said second inner wall surface is parallel to said first inner wall surface.

3. A dual lumen catheter as recited in claim 2, wherein in a transverse cross section of said catheter body taken normal to said longitudinal axis thereof, said cross section of said second lumen comprises:

(a) a generally linear first inner wall surface of said second set of inner wall surfaces; and (b) a generally linear second inner wall surface of said second set of inner wall surfaces, said second inner wall surface being parallel to said first inner wall surface, and the length of said first inner wall surface of said second set of inner wall surfaces being less than the length of said second inner wall surface of said second set of inner wall surfaces.

4. A dual lumen catheter as recited in claim 3, wherein said second inner wall surface of said first set of inner wall surfaces is parallel to said second inner wall surface of said second set of inner wall surfaces.

5. A dual lumen catheter as recited in claim 1, wherein said first set of longitudinally extending inner wall surfaces and said second set of longitudinally extending inner wall surfaces each comprise four linear inner wall surfaces.

6. A dual lumen catheter as recited in claim 1, wherein said first set of longitudinally extending inner wall surfaces and said second set of longitudinally extending inner wall surfaces each comprise five linear inner wall surfaces.

7. A dual lumen catheter as recited in claim 1, wherein in a transverse cross section of said catheter body taken normal to said longitudinal axis thereof, the cross section of each of said first lumen and said second lumen assumes a trapezoidal shape.

8. A dual lumen catheter as recited in claim 1, wherein said first valve means comprises a longitudinally extending slit formed in said catheter body extending from said exterior surface thereof to said first lumen.

9. A dual lumen catheter as recited in claim 1, wherein said first valve means comprises a two-way, three-position valve associated with said first lumen at said distal end of said catheter body, said first valve being biased into a closed position thereof in which fluid communication is precluded between said first lumen and the exterior of said catheter body, and said first valve being selectively operable from said closed position thereof into either an inwardly or an outwardly open position, said valve comprising:

(i) a slit formed in said catheter body extending from said exterior surface thereof to said first lumen, said slit defining opposed first and second slit faces that sealingly engage each other in said closed position of said first valve; and (ii) an operative valve wall comprising a portion of said catheter body adjacent said first slit face, said operative valve wall being flexible inward into said first lumen in said inwardly open position of said slit valve and flexible outward into the exterior of said catheter body in said outwardly open position of said valve.

10. A dual lumen catheter as recited in claim 1, further comprising second valve means associated with said second lumen at said distal end of said catheter body (1) for selectively infusing a fluid from said second lumen to said exterior of said catheter body, (2) for selectively withdrawing fluid through said second lumen from said exterior surface of said catheter body, and (3) for selectively precluding fluid communication between said second lumen and said exterior surface of said catheter body.

11. A dual lumen catheter implantable in the body of a patient in fluid communication with the fluid reservoirs of a dual reservoir access port, the access port having an outlet stem that includes a pair of parallel outlet prongs projecting outwardly from the body of the access port, each of the outlet prongs having an inner surface opposing the other of the outlet prongs, thereby to define between the inner surfaces a slot in the outlet stem, said catheter comprising:

(a) an elongated catheter body of elastomeric material having a longitudinal axis, an exterior surface, a distal end, and an open proximal end;

(b) a first lumen longitudinally extending through said catheter body from said proximal end to said distal end thereof, said first lumen in a transverse cross section of said catheter body taken normal to the longitudinal access thereof assuming a trapezoidal shape, said first trapezoidal shape assumed by first lumen comprising:

(i) a first generally linear inner wall surface; and (ii) a second generally linear inner wall surface parallel to said first inner wall surface, the length of said first inner wall surface of said first lumen being less than the length of said second inner wall surface of said first lumen;

(c) a second lumen longitudinally extending through said catheter body from said proximal end to said distal end thereof, said second lumen in said transverse cross section of said catheter body assuming a second trapezoidal shape, said second trapezoidal shape assumed by said second lumen comprising:

(i) a first generally linear inner wall surface; and (ii) a second generally linear inner wall surface parallel to said first inner wall surface, the length of said first inner wall surface of said second lumen being less than the length of said second inner wall surface of said second lumen; and (d) a septum separating said first lumen from said second lumen in said transverse cross section of said catheter body, said septum being defined on opposite sides thereof by said second inner wall surface of said first lumen and by said second inner wall surface of said second lumen, respectively.

12. A dual lumen catheter as recited in claim 11, wherein said trapezoidal shape of said first lumen and said trapezoidal shape of said second lumen are each isosceles trapezoidal shapes.

13. A dual lumen catheter as recited in claim 11, wherein said second inner wall surface of said first lumen is parallel to said second inner wall surface of said second lumen.

14. A dual lumen catheter as recited in claim 11, wherein said first lumen and said second lumen are sized to snugly receive individual of the outlet prongs.

15. A dual lumen catheter as recited in claim 11, wherein said septum substantially fills the slot in the outlet stem when the outlet prongs are received in said first lumen and said second lumen, respectively.

16. A dual lumen catheter as recited in claim 11, wherein said first lumen is defined by a plurality of generally linear inner wall surfaces, and adjacent of said inner wall surfaces are interconnected at junctures, each of said junctures when viewed in said transverse cross section of said catheter body comprising an arcuate fillet tangentially interconnecting said adjacent of said linear inner wall surfaces.

17. A dual lumen catheter as recited in claim 11, wherein said first lumen is defined by a plurality of generally linear inner wall surfaces, and adjacent of said inner wall surfaces are interconnected at junctures, each of said junctures when viewed in said transverse cross section of said catheter body comprising a straight section interconnecting said adjacent of said linear inner wall surfaces.

18. A dual lumen catheter as recited in claim 11 further comprising a valve means associated with said first lumen at said distal end of said catheter body (1) for selectively infusing fluid from said first lumen to the exterior of said catheter body, (2) for selectively withdrawing fluid through said first lumen from the exterior of said catheter body, and (3) for selectively precluding fluid communication between said first lumen and the exterior of said catheter body.

19. A dual lumen catheter as recited in claim 18, wherein said valve means comprises a longitudinally extending slit formed in said catheter body extending from said exterior surface thereof to said first lumen through said first inner wall surface thereof.

20. A dual lumen catheter as recited in claim 19, wherein said slit is asymmetrically disposed in said first inner wall surface when viewed in said transverse cross section of said catheter body.

21. A multiple lumen catheter implantable in the body of a patient in fluid communication with the fluid reservoirs of a dual reservoir access port, the access port having an outlet stem that includes a plurality of parallel outlet prongs projecting outwardly from the body of the access port, each of the outlet prongs having an inner surface opposing another of the plurality of the outlet prongs, thereby to define between the inner surfaces a slot in the outlet stem, said catheter comprising:

(a) an elongated catheter body of elastomeric material having a longitudinal axis, an exterior surface, a closed distal end, and an open proximal end;

(b) a first lumen longitudinally extending through said catheter body from said proximal end to said distal end thereof and being defined by a first set of longitudinally extending inner wall surfaces, said first set of longitudinally extending inner wall surfaces when viewed in a transverse cross section of said catheter body taken normal to said longitudinal axis thereof comprising:

(i) a generally linear first inner wall surface; and (ii) a generally linear second inner wall surface parallel to said first inner wall surface, the length of said first inner wall surface of said first set of inner wall surfaces being less than the length of said second inner wall surface of said first lumen;

(c) a first two-way, three-position valve associated with said first lumen at said distal end of said catheter body, said first valve being biased into a closed position thereof in which fluid communication is precluded between said first lumen and the exterior of said catheter body, and said first valve being selectively operable from said closed position thereof into either an inwardly or an outwardly open position, said first valve comprising:

(i) a slit formed in said catheter body extending from said exterior surface thereof to said first lumen through said first inner wall surface thereof, said slit defining opposed first and second slit faces that sealingly engage each other in said closed position of said first valve; and (ii) an operative valve wall comprising a portion of said catheter body adjacent said first slit face, said operative valve wall being flexible inward into said first lumen in said inwardly open position of said first valve and flexible outward into the exterior of said catheter body in said outwardly open position of said first valve;

(d) a second lumen longitudinally extending through said catheter body from said proximal end to said distal end thereof and being defined by a second set of longitudinally extending inner wall surfaces; and (e) sealing means formed by said first set of inner wall surfaces and said second set of inner wall surfaces at said proximal end of said catheter body for effecting a fluid tight mechanical engagement between the outlet stem of the access port and each of said first lumen and said second lumen.

22. A multiple lumen catheter as recited in claim 21, wherein said first inner wall surface of said first set of inner wall surfaces forms a juncture at each end thereof with respective individual ones of said first set of inner wall surfaces located adjacent thereto, and said slit extends through said first inner wall surface adjacent to one of said junctures.

23. A multiple lumen catheter as recited in claim 22, wherein said slit when viewed in said transverse cross section of said catheter body is substantially perpendicular to said first inner wall surface.

24. A multiple lumen catheter as recited in claim 21, wherein in said transverse cross section of said catheter body, the cross section of said first lumen assumes a trapezoidal shape.

25. A multiple lumen catheter as recited in claim 21, wherein the length of said second inner wall surface of said first set of inner wall surfaces is less than or equal to the width of the inner surfaces of the outlet prongs of the outlet stem.

26. A multiple lumen catheter as recited in claim 25, wherein the length of said second inner wall surface of said first set of inner wall surfaces is less than the width of the inner surfaces of the outlet prongs of the outlet stem.

27. A multiple lumen catheter as recited in claim 26, the slot in the outlet stem is substantially filled by material of the catheter body when outlet prongs of the outlet stem are received in said first lumen and in said second lumen, respectively.

28. A dual lumen catheter as recited in claim 21, further comprising a second two-way, three-position valve associated with said second lumen at said distal end of said catheter body, said second valve being biased into a closed position thereof in which fluid communication is precluded between said second lumen and the exterior of said catheter body, and said second valve being selectively operable from said closed position thereof into either an inwardly or an outwardly open position, said second valve comprising:

(a) a slit formed in said catheter body extending from said exterior surface thereof to said second lumen, said slit defining opposed first and second slit faces that sealingly engage each other in said closed position of said second valve; and (b) an operable valve wall comprising a portion of said catheter body adjacent said first slit face, said operable valve wall being flexible inward into said second lumen in said inwardly open position of said second valve and flexible outward into the exterior of said catheter body in said outwardly open position of said second valve.

29. A multiple lumen catheter tube comprising:

(a) an elongated catheter body of elastomeric material having a longitudinal axis and an exterior surface;

(b) a first lumen longitudinally extending through said catheter body, said first lumen when viewed in a transverse cross section of said catheter body taken normal to said longitudinal axis being defined by a first plurality of longitudinally extending, generally linear inner wall surfaces, said inner wall surfaces comprising:
  (i) a first inner wall surface; and
  (ii) a second inner wall surface nonadjacent to said first inner wall surface in said transverse cross section of said catheter body, the length of said first inner wall surface of said first lumen being less than the length of said second inner wall surface of said first lumen;
(c) a second lumen longitudinally extending through said catheter body, said second lumen when viewed in said transverse cross section of said catheter body taken normal to said longitudinal axis being defined by a second plurality of longitudinally extending, generally linear inner wall surfaces, said inner wall surfaces comprising:
  (i) a first inner wall surface; and
  (ii) a second inner wall surface nonadjacent to said first inner wall surface in said transverse cross section of said catheter body, the length of said first inner wall surface of said second lumen being less than the length of said second inner wall surface of said second lumen.

30. A multiple lumen catheter tube as recited in claim 29, wherein said second inner wall surface of said first lumen is parallel to said second inner wall surface of said second lumen.

31. A multiple lumen catheter tube as recited in claim 29, wherein none of said first plurality of inner wall surfaces are parallel to each other.

32. A multiple lumen catheter tube as recited in claim 29, wherein said first plurality of inner wall surfaces comprises four inner wall surfaces.

33. A multiple lumen catheter tube as recited in claim 29, wherein said first plurality of inner wall surfaces comprises five inner wall surfaces.

34. A multiple lumen catheter tube as recited in claim 29, wherein said first lumen when viewed in said transverse cross section of said catheter body assumes a trapezoidal shape.

35. A multiple lumen catheter tube as recited in claim 29, wherein the cross section of said first lumen when viewed in said transverse cross section of said catheter body is geometrically similar to the cross section of said second lumen.

36. A multiple lumen catheter tube as recited in claim 35, wherein the cross section of said first lumen when viewed in said transverse cross section of said catheter body is geometrically congruent to the cross section of said second lumen.

37. A multiple lumen catheter tube as recited in claim 29, wherein the cross section of said first lumen when viewed in said transverse cross section of said catheter body is geometrically congruent to the cross section of said second lumen.

38. A catheter tube comprising:
(a) an elongated catheter body of elastomeric material having a longitudinal axis and an exterior surface;
(b) a first lumen longitudinally extending through said catheter body, said first lumen being defined by a first plurality of longitudinally extending inner wall surfaces, said first lumen when viewed in a transverse cross section of said catheter body taken normal to said longitudinal axis thereof comprising:
  (i) a generally linear first inner wall surface; and
  (ii) a generally linear second inner wall surface parallel to said first inner wall surface, the length of said first inner wall surface of said first lumen being less than the length of said second inner wall surface of said first lumen;
(c) a second lumen longitudinally extending through said catheter body, said second lumen being defined by a second plurality of longitudinally extending inner wall surfaces, said second lumen when viewed in said transverse cross section of said catheter body taken normal to said longitudinal axis thereof comprising:
  (i) a generally linear first inner wall surface; and
  (ii) a generally linear second inner wall surface parallel to said first inner wall surface, the length of said first inner wall surface being less than the length of said second inner wall surface of said second lumen.

39. A catheter tube as recited in claim 38, wherein in said transverse cross section of said catheter body said first inner wall surface of said first lumen is located on the side of said first lumen remote from said second lumen.

40. A catheter tube as recited in claim 39, wherein in said transverse cross section of said catheter body said first inner wall surface of said second lumen is located on the side of said second lumen remote from said first lumen, thereby to define between said first lumen and said second lumen a septum bounded on opposite sides thereof by said second inner wall surface of said first lumen and said second inner wall surface of said second lumen.

41. A catheter tube as recited in claim 40, wherein in said transverse cross section of said catheter body said second inner wall surface of said first lumen is parallel to said second inner wall surface of said second lumen.

42. A catheter tube as recited in claim 40, wherein in said transverse cross section of said catheter body said second inner wall surface of said first lumen and said second inner wall surface of said second lumen are nonparallel.

43. A catheter tube as recited in claim 40, further comprising a third lumen longitudinally extending through said catheter body, said third lumen when viewed in said transverse cross section of said catheter body having a circular cross section.

44. A catheter tube as recited in claim 38, wherein in said transverse cross section of said catheter body said second inner wall surface of said first lumen is located on the side of said first lumen remote from said second lumen.

45. A catheter tube as recited in claim 44, wherein in said transverse cross section of said catheter body said second inner wall surface of said second lumen is located on the side of said second lumen remote from said first lumen, thereby to define between said first lumen and said second lumen a septum bounded on opposite sides thereof by said first inner wall surface of said first lumen and said first inner wall surface of said second lumen.

46. A catheter tube as recited in claim 45, wherein in said transverse cross section of said catheter body said first inner wall surface of said first lumen is parallel to said first inner wall surface of said second lumen.

47. A catheter tube as recited in claim 38, wherein in said transverse cross section of said catheter body said first lumen and said second lumen each assumes a trapezoidal shape.

48. A catheter as recited in claim 38, wherein in said transverse cross section of said catheter body said first lumen is geometrically similar to said second lumen.

49. A catheter as recited in claim 48, wherein in said transverse cross section of said catheter body said first lumen is geometrically congruent to said second lumen.

50. A catheter as recited in claim 38, wherein said first plurality of longitudinally extending inner wall surfaces of said first lumen comprises four inner wall surfaces.

51. A catheter as recited in claim 38, wherein said first plurality of longitudinally extending inner wall surfaces of said first lumen comprises five inner wall surfaces.

52. A catheter tube as recited in claim 38, wherein one end of said catheter body is closed.

53. A catheter tube as recited in claim 52, wherein a plug of material is received in one end of each of said first lumen and said second lumen, thereby to close said one end of each of said first lumen and second lumen.

54. A catheter tube as recited in claim 53, wherein said catheter body further comprises:
(a) a first longitudinally extending slit formed through said catheter body extending from said exterior surface thereof to said first lumen; and
(b) a second longitudinally extending slit formed through said catheter body extending from said exterior surface thereof to said second lumen.

55. A catheter tube as recited in claim 53, wherein in said transverse cross section said exterior of said catheter body thereof is circular.

56. A catheter tube comprising:
(a) an elongated catheter body of elastomeric material having a longitudinal axis and an exterior surface;
(b) a lumen longitudinally extending through said catheter body, said lumen being defined by a plurality of longitudinally extending inner wall surfaces, said lumen in a transverse cross section of said catheter body taken normal to said longitudinal axis thereof comprising:
(i) a generally linear first inner wall surface; and
(ii) a generally linear second inner wall surface nonadjacent to said first inner wall surface in said transverse cross section of said catheter body, the length of said first inner wall surface being less than the length of said second inner wall surface.

57. A catheter tube as recited in claim 56, wherein said lumen when viewed in said transverse cross section of said catheter body assumes a trapezoidal shape.

58. A catheter tube as recited in claim 57, wherein said trapezoidal shape is isosceles.

59. A catheter tube as recited in claim 56, wherein said plurality of inner wall surfaces comprise four inner wall surfaces.

60. A catheter tube as recited in claim 56, wherein said plurality of inner wall surfaces comprise five inner wall surfaces.

61. A catheter tube as recited in claim 56, wherein adjacent of said plurality of inner wall surfaces are interconnected at a juncture, and said juncture when viewed in said transverse cross section of said catheter body comprises an arcuate fillet tangentially interconnecting said adjacent of said plurality of inner wall surfaces.

62. A catheter tube as recited in claim 56, wherein adjacent of said plurality of inner wall surfaces are interconnected at a juncture, and said juncture when viewed in said transverse cross section of said catheter body comprises a straight section interconnecting said adjacent of said plurality of inner wall surfaces.

63. A catheter tube as recited in claim 56, further comprising a plug of material received in and closing said lumen at one end of said catheter body.

64. A catheter tube as recited in claim 63, further comprising a slit longitudinally formed in said catheter body at said one end thereof extending from said exterior surface of said catheter body to said lumen.

65. A catheter tube as recited in claim 64, wherein in said transverse cross section of said catheter body said slit extends to said lumen through said first inner wall surface and is perpendicular to said first inner wall surface.

66. A catheter tube as recited in claim 64, wherein the shape of said lumen in a transverse cross section of said catheter body at any location therealong is congruent to the shape of said lumen in a transverse cross section of said catheter body at said slit.

67. A catheter tube as recited in claim 64, wherein said slit has a length in a range of from about 0.250 inches to about 0.450 inches.

68. A catheter tube as recited in claim 67, wherein said slit has a length in a range of from about 0.400 inches to about 0.450 inches.

69. A catheter tube as recited in claim 67, wherein said slit has a length in a range of from about 0.325 inches to about 0.375 inches.

70. A catheter tube as recited in claim 67, wherein said slit has a length in a range of from about 0.250 inches to about 0.300 inches.

71. A catheter tube as recited in claim 56, wherein said elastomeric material of said catheter body has a durometer in a range of from about 50 to about 80.

72. A catheter tube as recited in claim 71, wherein said elastomeric material of said catheter body has a durometer in a range of from about 60 to about 70.

73. A catheter tube as recited in claim 56, wherein said first inner wall surface is parallel to said second inner wall surface.

74. A catheter tube as recited in claim 56, wherein said plurality of inner wall surfaces comprises six inner wall surfaces.

75. A multiple lumen catheter tube comprising:
(a) an elongated catheter body of elastomeric material having a longitudinal axis and an exterior surface;
(b) a plurality of lumens longitudinally extending through said catheter body, each of said plurality of lumens when viewed in a transverse cross section of said catheter body taken normal to said longitudinal axis being defined by a plurality of longitudinally extending, generally linear inner wall surfaces, said inner wall surfaces corresponding to each of said plurality of lumens comprising:
(i) a first inner wall surface; and
(ii) a second inner wall surface nonadjacent to said first inner wall surface in said transverse cross section of said catheter body, the length of said first inner wall surface being less than the length of said second inner wall surface.

76. A multiple lumen catheter tube as recited in claim 75, wherein each of said plurality of lumens when viewed in said transverse cross section of said catheter body assumes a trapezoidal shape.

77. A multiple lumen catheter tube as recited in claim 76, wherein in said transverse cross section of said catheter body said first inner wall surface of each of said plurality of lumens is disposed on the side of the corresponding one of said plurality of lumens opposite from said exterior surface of said catheter body.

78. A catheter tube as recited in claim 76, wherein in said transverse cross section of said catheter body said second inner surface of each of said plurality of lumens is disposed on the side of the corresponding one of said plurality of lumens opposite from said exterior surface of said catheter body.

79. A multiple lumen catheter tube as recited in claim 75, wherein the cross section of each of said plurality of lumens when viewed in said transverse cross section of said catheter body is geometrically similar to the cross sections of the other of said plurality of lumens.

80. A multiple lumen catheter as recited in claim 79, wherein the cross section of each of said plurality of lumens when viewed in said transverse cross section of said catheter body is geometrically congruent to the cross sections of the other of said plurality of lumens.

81. A multiple lumen catheter as recited in claim 75, wherein said plurality of lumens comprises two lumens.

82. A multiple lumen catheter as recited in claim 75, wherein said plurality of lumens comprises three lumens.

83. A multiple lumen catheter tube as recited in claim 75, further comprising a circular lumen longitudinally extending through said catheter body, said circular lumen being distinct from said plurality of lumens.

* * * * *